United States Patent
Abe

(10) Patent No.: US 11,123,043 B2
(45) Date of Patent: Sep. 21, 2021

(54) ULTRASOUND DIAGNOSTIC APPARATUS, MEDICAL IMAGE PROCESSING APPARATUS, AND MEDICAL IMAGE PROCESSING METHOD

(71) Applicant: Toshiba Medical Systems Corporation, Otawara (JP)

(72) Inventor: Yasuhiko Abe, Otawara (JP)

(73) Assignee: CANON MEDICAL SYSTEMS CORPORATION, Otawara (JP)

(*) Notice: Subject to any disclaimer, the term of this patent is extended or adjusted under 35 U.S.C. 154(b) by 514 days.

(21) Appl. No.: 15/657,669

(22) Filed: Jul. 24, 2017

(65) Prior Publication Data
US 2018/0028155 A1 Feb. 1, 2018

(30) Foreign Application Priority Data
Jul. 26, 2016 (JP) .............................. JP2016-146713

(51) Int. Cl.
*A61B 8/08* (2006.01)
*G06T 11/20* (2006.01)
(Continued)

(52) U.S. Cl.
CPC ............ *A61B 8/5207* (2013.01); *A61B 8/065* (2013.01); *A61B 8/0883* (2013.01); *A61B 8/469* (2013.01);
(Continued)

(58) Field of Classification Search
CPC ......... A61B 8/08; A61B 8/065; A61B 8/5223; A61B 8/5207; A61B 8/488; A61B 8/469;
(Continued)

(56) References Cited

U.S. PATENT DOCUMENTS 6,187,032 B1 2/2001 Ohyu et al.
8,077,944 B2 * 12/2011 Schummers .......... G06F 19/321
382/128

(Continued)

FOREIGN PATENT DOCUMENTS

| JP | 11-128191 | 5/1999 |
| JP | 2010-537701 | 12/2010 |
| JP | 2016-101482 | 6/2016 |

OTHER PUBLICATIONS

Zhong ["Right ventricular regional wall curvedness and area strain in patients with repaired tetralogy of Fallot" Am. J. Physiol Heart Circ Physiol 302: H1306-H1316, 2012.] (Year: 2012).*

(Continued)

*Primary Examiner* — Oommen Jacob
(74) *Attorney, Agent, or Firm* — Oblon, McClelland, Maier & Neustadt, L.L.P.

(57) ABSTRACT

An ultrasound diagnostic apparatus according to one embodiment includes processing circuitry. The processing circuitry acquires local function index values related to a right ventricle. The processing circuitry generates a functional image of the right ventricle representing a distribution of the local function index values, using a medical model diagram of the right ventricle, the medical model diagram being a model diagram in which the right ventricle is developed onto a plane, and in which a blood inlet portion leading into the right ventricle and a blood outflow portion leading out from the right ventricle are plotted to positions that are separated from each other on the external circumference side of the model diagram. The processing circuitry then causes a display to display the functional image of the right ventricle.

24 Claims, 18 Drawing Sheets

(51) Int. Cl.
*A61B 8/06* (2006.01)
*A61B 8/00* (2006.01)
*G06T 7/00* (2017.01)
*A61B 8/14* (2006.01)

(52) U.S. Cl.
CPC .............. *A61B 8/483* (2013.01); *A61B 8/488* (2013.01); *A61B 8/5223* (2013.01); *G06T 7/0012* (2013.01); *G06T 11/206* (2013.01); *A61B 8/14* (2013.01); *A61B 8/463* (2013.01); *A61B 8/466* (2013.01); *A61B 8/486* (2013.01); *A61B 8/5261* (2013.01); *A61B 8/5284* (2013.01); *A61B 8/565* (2013.01); *G06T 2207/10081* (2013.01); *G06T 2207/10088* (2013.01); *G06T 2207/10132* (2013.01); *G06T 2207/30048* (2013.01); *G06T 2207/30104* (2013.01)

(58) Field of Classification Search
CPC ....... A61B 8/0883; A61B 8/483; A61B 8/565; A61B 8/5284; A61B 8/5261; A61B 8/486; A61B 8/463; A61B 8/14; A61B 8/466; A61B 8/0891; A61B 8/461–463; A61B 8/48–488; G06T 7/0012; G06T 11/206; G06T 2207/10132; G06T 2207/10088; G06T 2207/10081; G06T 2207/30048; G06T 2207/30104
USPC ........ 600/456, 455, 454, 453, 443, 437, 441
See application file for complete search history.

(56) References Cited

U.S. PATENT DOCUMENTS

| | | | | |
|---|---|---|---|---|
| 9,064,300 | B2* | 6/2015 | Fritz | G06T 7/0012 |
| 2004/0192705 | A1* | 9/2004 | Burns | A61K 51/0459 |
| | | | | 514/256 |
| 2006/0045328 | A1* | 3/2006 | Jacob | G06T 11/206 |
| | | | | 382/154 |
| 2006/0253033 | A1* | 11/2006 | Nair | A61B 5/02007 |
| | | | | 600/467 |
| 2007/0167777 | A1* | 7/2007 | Abe | A61B 8/463 |
| | | | | 600/441 |
| 2008/0008366 | A1* | 1/2008 | Desh | G06T 19/00 |
| | | | | 382/128 |
| 2008/0262814 | A1* | 10/2008 | Zheng | G06F 19/34 |
| | | | | 703/11 |
| 2008/0273782 | A1* | 11/2008 | Ichihara | A61B 5/0275 |
| | | | | 382/131 |
| 2008/0292169 | A1* | 11/2008 | Wang | G06T 7/0012 |
| | | | | 382/131 |
| 2008/0310580 | A1* | 12/2008 | Takahashi | A61B 6/037 |
| | | | | 378/4 |
| 2010/0201687 | A1 | 8/2010 | Breeuwer et al. | |
| 2010/0280355 | A1* | 11/2010 | Grimm | A61B 5/02028 |
| | | | | 600/411 |
| 2012/0063663 | A1* | 3/2012 | Kawasaki | G06T 7/0014 |
| | | | | 382/133 |
| 2012/0165674 | A1* | 6/2012 | Abe | A61B 8/0883 |
| | | | | 600/443 |
| 2014/0243641 | A1* | 8/2014 | Boveja | A61B 5/0472 |
| | | | | 600/374 |
| 2015/0173698 | A1* | 6/2015 | Sakaguchi | A61B 6/12 |
| | | | | 378/62 |
| 2015/0206302 | A1* | 7/2015 | Chen | G06T 7/0012 |
| | | | | 382/131 |
| 2016/0140707 | A1 | 5/2016 | Abe et al. | |
| 2018/0028155 | A1* | 2/2018 | Abe | A61B 8/065 |

OTHER PUBLICATIONS

Bart ["Detection and Quantification by Deformation Imaging of the Functional Impact of Septal Compared to Free Wall Preexcitation in the Wolff-Parkinson-White Syndrome", The American Journal of Cardiology, 2010], (Year: 2010).*

Thomas ["Anatomy of the Crista Supraventricularis: Its Importance for Understanding Right Ventricular Function, Right Ventricular Infarction and Related Conditions" IACC vol. 6, No. 5 Nov. 1985: 1083-95] (Year: 1985).*

Morris ["The Interventricular Septum" Thorax (1957), 12, 304.] (Year: 1957).*

Maron ["Clinical Utility of Cardiovascular Magnetic Resonance in Hypertrophic Cardiomyopathy" Journal of Cardiovascular Magnetic Resonance 2012,] (Year: 2012).*

U.S. Appl. No. 14/934,647, filed Nov. 6, 2015, 2016/0140707 A1, Tomoya Okazaki, et al.

U.S. Appl. No. 15/657,669, filed Jul. 24, 2017, Yasuhiko Abe.

Liang Zhong, et al. "Right ventricular regional wall curvedness and area strain in patients with repaired tetralogy of Fallot", American Journal of Physiology: Heart and Circulatory Physiology, 2012, vol. 302, No. 6, 12 pages.

Francois Haddad, et al. "Right Ventricular Function in Cardiovascular Disease, Part I: Anatomy, Physiology, Aging, and Functional Assessment of the Right Ventricle", Circulation, 2008, vol. 117, No. 11, 14 pages.

Manuel D. Cerqueira, et al. "Standardized Myocardial Segmentation and Nomenclature for Tomographic Imaging of the Heart", Circulation, 2002, vol. 105, No. 4, 5 pages.

Roberto M. Lang, et al. "Recommendations for Chamber Quantification: A Report from the American Society of Echocardiography's Guidelines and Standards Committee and the Chamber Quantification Writing Group, Developed in Conjunction with the European Association of Echocardiography, a Branch of the European Society of Cardiology", Journal of the American Society of Echocardiography, 2015, vol. 18,No. 12, 24 pages.

Keiko Ryo, et al. "Characterization of Right Ventricular Remodeling in Pulmonary Hypertension Associated With Patient Outcomes by 3-Dimensional Wall Motion Tracking Echocardiography", Circulation: Cardiovascular Imaging, 2015, vol. 8, No. 6, 10 pages.

Akiko Atsumi, et al. "Right Ventricular Deformation Analyses Using a Three-Dimensional Speckle-Tracking Echocardiographic System Specialized for the Right Ventricle", Journal of the American Society of Echocardiography, 2016, vol. 29, No. 5, 12 pages.

T. Ishizu, et al. "Right Ventricular Area Strain as the New Indicator for Right Ventricular Systolic Function", The 80$^{th}$ Annual Scientific Meeting of the Japanese Circulation Society, 2016, 3 pages.

Alberto Gomez, et al. "Regional Differences in End-Diastolic Volumes between 3D Echo and CMR in HLHS Patients", Frontiers in Pediatrics, 2016, vol. 4, No. 133, 8 pages.

* cited by examiner

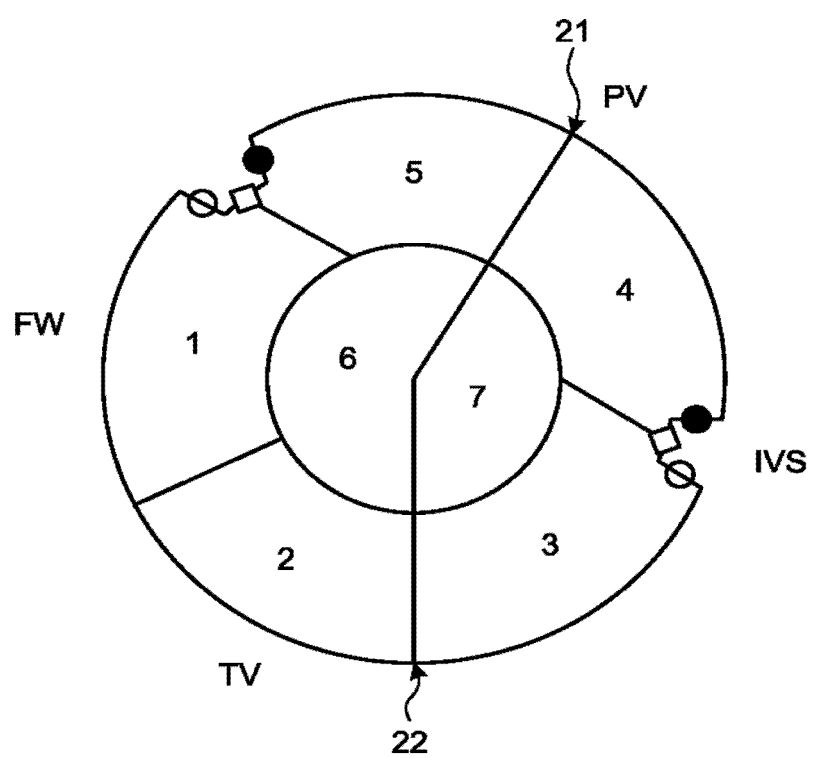

segmental RV Polar-map
with development view
& connection-marker segmental RV Polar-map
without development view

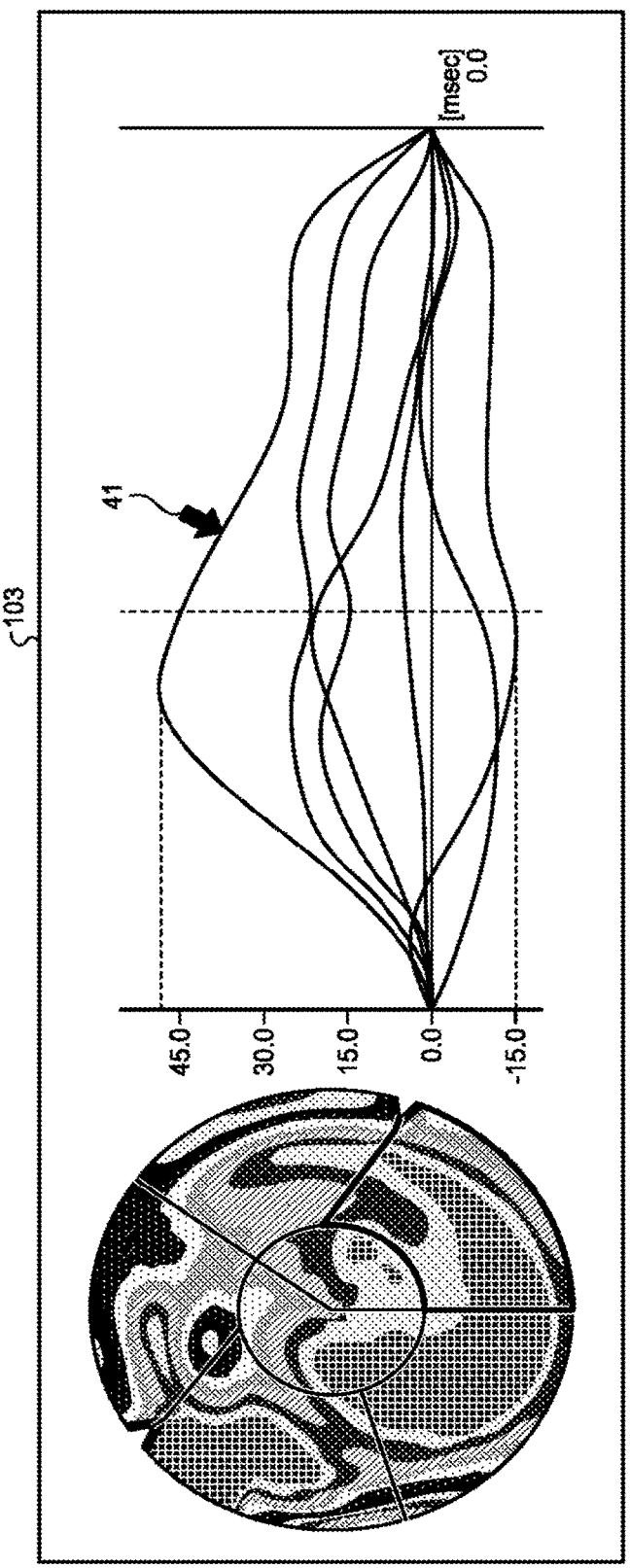

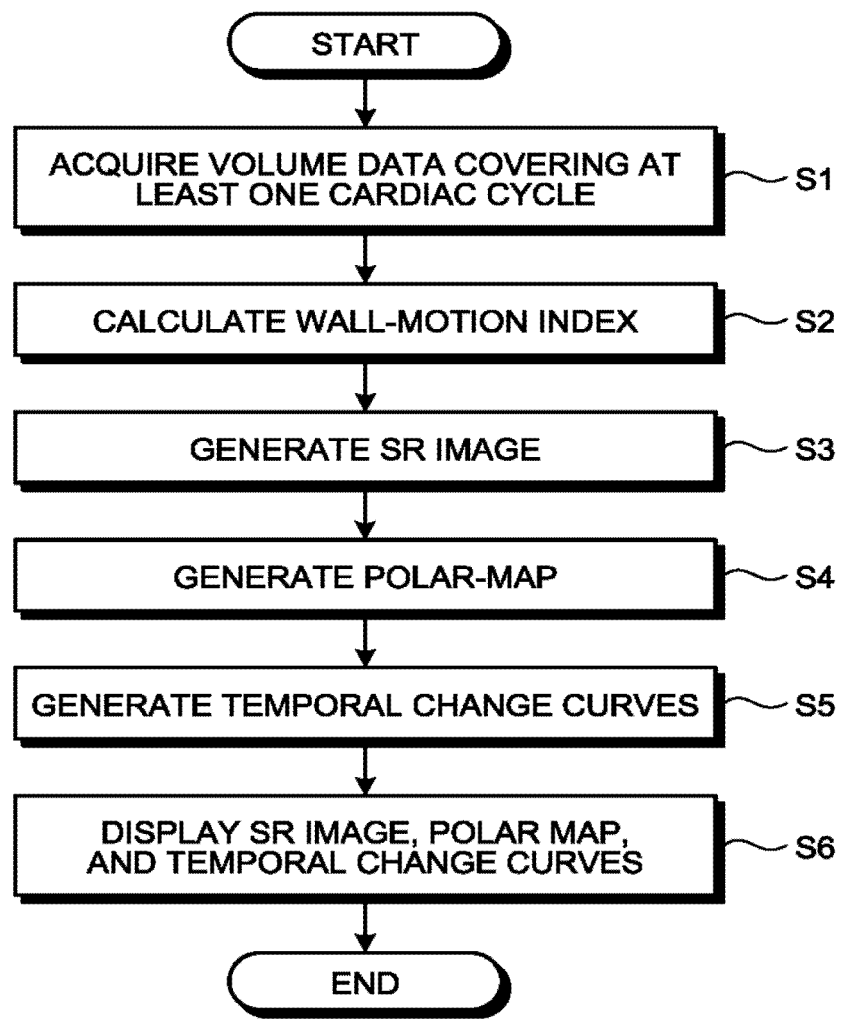

ULTRASOUND DIAGNOSTIC APPARATUS, MEDICAL IMAGE PROCESSING APPARATUS, AND MEDICAL IMAGE PROCESSING METHOD

CROSS-REFERENCE TO RELATED APPLICATIONS

This application is based upon and claims the benefit of priority from Japanese Patent Application No. 2016-146713, filed on Jul. 26, 2016; the entire contents of which are incorporated herein by reference.

FIELD

Embodiments described herein relate generally to an ultrasound diagnostic apparatus, a medical image processing apparatus, and a medical image processing method.

BACKGROUND

Conventionally, in the field of three-dimensional tracking (3DT) for analyzing the wall-motion index of a heart three-dimensionally, visual presentations such as a three-dimensional image, resultant of a surface rendering (SR) process (hereinafter, referred to as an SR image), or a polar-map have been generally used.

An SR image is an image having a plurality of regions of interest resultant of dividing a three-dimensional image generated using volume data of a left cardiac ventricle, and having a wall-motion index assigned to each of such regions of interest, for example. Such an SR image provides shape information, but is not quite perspicuous, because the side opposite to a viewpoint of a user is hidden, and cannot be seen simultaneously.

By contrast, a polar-map is an image in which the wall-motion indices, such as displacements or distortions of tissues in the left ventricle (LV), are developed onto a two-dimensional plane, with the cardiac apex at the pole. Therefore, with a visual presentation using a polar-map, users can get a grasp of the entire appearance of the left ventricle, and examine a local distribution of the function indices, or gain the entire view at one glance. Also known is a technology for outputting a curve representing temporal changes of the wall-motion indices corresponding to a plurality of respective segments, based on a segment model of a left ventricle that is recommended by the American Society of Echocardiography (ASE)/American Heart Association (AHA), and that is often used in nuclear medical diagnostic apparatuses.

BRIEF DESCRIPTION OF THE DRAWINGS

FIG. 5C is another schematic for explaining the first embodiment;

FIG. 11 is another schematic for explaining the first embodiment;

FIG. 12 is a flowchart illustrating a process performed by the ultrasound diagnostic apparatus according to the first embodiment;

DETAILED DESCRIPTION

An ultrasound diagnostic apparatus, a medical image processing apparatus, and a medical image processing method according to some embodiments will now be explained with reference to some drawings. The embodiment is, however, not limited to those described below. Furthermore, the description in one of the embodiment is, in principle, also applicable to any other embodiments.

An ultrasound diagnostic apparatus according to one embodiment includes processing circuitry. The processing circuitry acquires local function index values related to a right ventricle. The processing circuitry generates a functional image of the right ventricle representing a distribution of the local function index values, using a medical model diagram of the right ventricle, the medical model diagram being a model diagram in which the right ventricle is developed onto a plane, and in which a blood inlet portion leading into the right ventricle and a blood outflow portion leading out from the right ventricle are plotted to positions that are separated from each other on the external circumference side of the model diagram. The processing circuitry then causes a display to display the functional image of the right ventricle.

First Embodiment

A configuration of an ultrasound diagnostic apparatus according to a first embodiment will now be explained. FIG.

Figure 1:
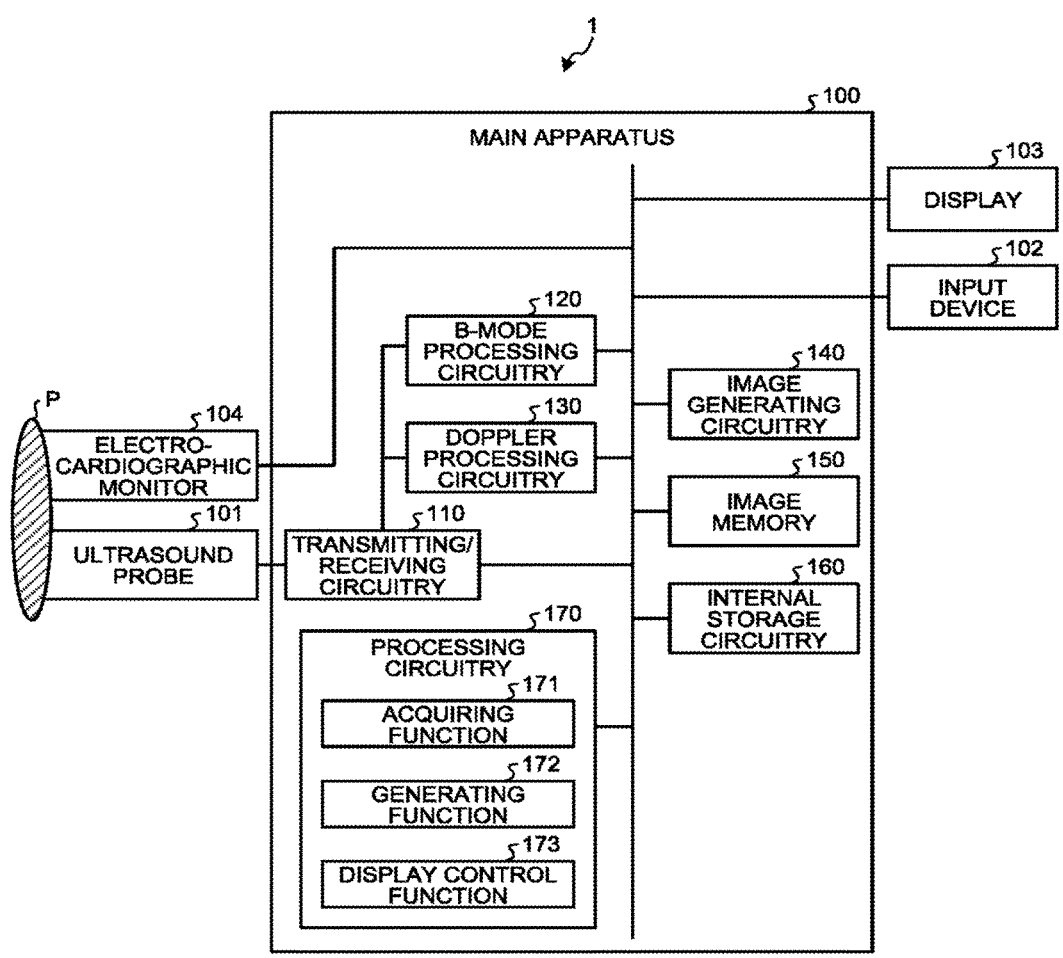
FIG. 1 is a block diagram illustrating an exemplary configuration of an ultrasound diagnostic apparatus according to a first embodiment.

1 is a block diagram illustrating an exemplary configuration of such an ultrasound diagnostic apparatus 1 according to the first embodiment. As illustrated in FIG. 1, the ultrasound diagnostic apparatus 1 according to the first embodiment includes a main apparatus 100, an ultrasound probe 101, an input device 102, a display 103, and an electrocardiographic monitor 104. The ultrasound probe 101, the input device 102, the display 103, and the electrocardiographic monitor 104 are communicatively connected to the main apparatus 100.

The ultrasound probe 101 has a plurality of piezoelectric transducer elements, and these piezoelectric transducer elements generate ultrasound based on driving signals supplied by transmitting/receiving circuitry 110 provided to the main apparatus 100. The ultrasound probe 101 also receives the reflection waves from the subject P, and converts reflection waves into electric signals. The ultrasound probe 101 also includes a matching layer provided to the piezoelectric transducer elements, and a backing material for preventing the ultrasound from propagating backwardly from the piezoelectric transducer elements. The ultrasound probe 101 is connected removably to the main apparatus 100.

Once the ultrasound is transmitted from the ultrasound probe 101 toward the subject P, the transmitted ultrasound is reflected one after another on a discontinuous acoustic impedance surface of the body tissues of the subject P, and is received by the piezoelectric transducer elements provided to the ultrasound probe 101 as reflection wave signals. The amplitudes of the received reflection wave signals are dependent on an acoustic impedance difference on the discontinuous surface on which the ultrasound is reflected. When the transmitted ultrasound pulse is reflected on a surface of moving blood flow or a moving cardiac wall, for example, the frequency of a resultant reflection wave signal will be shifted due to the Doppler effect, based on the velocity component of the moving body with respect to the direction of the ultrasound transmission.

Used in the first embodiment is the ultrasound probe 101 too-dimensionally scanning the subject P with the ultrasound. An example of the ultrasound probe 101 is a 1D array probe on which a plurality of piezoelectric transducer elements are arranged along a line. Examples of the 1D array probe include a sector ultrasound probe, a linear ultrasound probe, and a convex ultrasound probe. In the first embodiment, the ultrasound probe 101 may also be a mechanical 4D probe capable of scanning the subject P three-dimensionally and two-dimensionally with the ultrasound, or a 2D array probe, for example. The mechanical 4D probe is not only capable of two-dimensional scanning with a plurality of piezoelectric transducer elements that are arranged along a line, but also three-dimensional scanning by swinging the piezoelectric transducer elements arranged along a line at a predetermined angle (swinging angle). The 2D array probe is not only capable of performing three-dimensional scanning using the piezoelectric transducer elements arranged in a matrix, but also capable of performing two-dimensional scanning by transmitting and receiving converged ultrasound. The 2D array probe is also capable of performing a two-dimensional scanning across a plurality of slices simultaneously.

The input device 102 is provided with a mouse, a keyboard, a button, a panel switch, a touch command screen, a foot switch, a trackball, a joystick, or the like, and receives various types of setting requests from an operator of the ultrasound diagnostic apparatus 1, and transfers the received various types of setting requests to the main apparatus 100.

The display 103 displays a graphical user interface (GUI) for allowing the operator of the ultrasound diagnostic apparatus 1 to enter various types of setting requests using the input device 102, or ultrasound image data or the like generated by the main apparatus 100. The display 103 also displays various types of messages in order to notify the operator of some processing status of the main apparatus 100. The display 103 also has a speaker, and is capable of outputting sound. For example, the speaker of the display 103 outputs predetermined sound such as beep sound in order to notify the operator of some processing status of the main apparatus 100.

The electrocardiographic monitor 104 acquires an electrocardiogram (ECG) of the subject P as a biological signal of the subject P who is to be two-dimensionally or three-dimensionally scanned. The electrocardiographic monitor 104 transmits the acquired ECG to the main apparatus 100. Explained in the embodiment is an example in which the electrocardiographic monitor 104 is used as means for acquiring the information related to the cardiac phase of the subject P, but the embodiment is not limited thereto. For example, the ultrasound diagnostic apparatus 1 may also acquire the information related to the cardiac phase of the subject P by acquiring the time at which the myocardial inner cavity volume, calculated by 3D speckle tracking (3DT) described later, is minimum, as an end-systolic time (ESt). The ultrasound diagnostic apparatus 1 may also acquire the information related to the cardiac phase of the subject P by acquiring the time of the II sounds (second sounds) in a phonocardiogram, or the aortic valve close (AVC) time that can be obtained by measuring the outflow of the heart using spectrum Doppler. It is also possible for the electrocardiographic monitor 104 not to be included in the ultrasound diagnostic apparatus 1.

The main apparatus 100 is an apparatus that generates ultrasound image data based on the reflection wave signal received by the ultrasound probe 101. The main apparatus 100 illustrated in FIG. 1 is an apparatus capable of generating two-dimensional ultrasound image data based on the two-dimensional reflection wave data received by the ultrasound probe 101.

The main apparatus 100 includes, as illustrated in FIG. 1, the transmitting/receiving circuitry 110, B-mode processing circuitry 120, Doppler processing circuitry 130, image generating circuitry 140, an image memory 150, internal storage circuitry 160, and processing circuitry 170.

The transmitting/receiving circuitry 110 includes a pulse generator, a transmission delaying unit, and a pulsar, and supplies a driving signal to the ultrasound probe 101. The pulse generator generates a rate pulse for forming the ultrasound to be transmitted, repeatedly at a predetermined rate frequency. The transmission delaying unit converges the ultrasound generated by the ultrasound probe 101 into a beam, and delays each rate pulse generated by the pulse generator by a delay time required for the transmission directivity to be determined, correspondingly to each of the piezoelectric transducer elements. The pulsar applies a driving signal (driving pulse) to the ultrasound probe 101 at the timing based on the rate pulse. In other words, the transmission delaying unit adjusts the direction of the ultrasound to be transmitted from the surface of the piezoelectric transducer elements, as required, by changing the delay time added to each of the rate pulses.

The transmitting/receiving circuitry 110 has a function for enabling the transmission frequency, the transmission driving voltage, and the like to be changed instantaneously so that a predetermined scanning sequence can be executed in accordance with an instruction from the processing circuitry 170 described later. In particular, the change in the transmission driving voltage is implemented by a linear amplifier type oscillator circuit capable of instantaneously changing its value, or by a mechanism electrically switching a plurality of power supply units.

The transmitting/receiving circuitry 110 also includes a preamplifier, an analog-to-digital (A/D) converter, a receiving delaying unit, and an adder, and generates reflection wave data by performing various types of processes to the reflection wave signals received by the ultrasound probe 101. The preamplifier amplifies a reflection wave signal for each channel. The A/D converter applies an A/D conversion to the amplified reflection wave signal. The receiving delaying unit delays the reflection wave signal by a delay time required for the reception directivity to be determined. The adder generates reflection wave data by adding the reflection wave signals processed by the receiving delaying unit. As a result of this addition performed by the adder, the reflection component corresponding to the direction that is based on the reception directivity of the reflection wave signal is emphasized, and a comprehensive beam for the ultrasound transmission and reception with the reception directivity and the transmission directivity is formed.

The transmitting/receiving circuitry 110 causes, when the subject P is to be scanned two-dimensionally, the ultrasound probe 101 to transmit a two-dimensional ultrasound beam. The transmitting/receiving circuitry 110 then generates the two-dimensional reflection wave data from the two-dimensional reflection wave signals received by the ultrasound probe 101.

Various types of output signals can be output from the transmitting/receiving circuitry 110, including what is called a radio frequency (RF) signal that is a signal including phase information, and amplitude information subsequent to an envelope detection process.

The B-mode processing circuitry 120 receives the reflection wave data from the transmitting/receiving circuitry 110, and generates data (B-mode data) in which signal intensities are represented as brightness of the luminance by performing processes such as logarithmic amplification and the envelope detection process.

The Doppler processing circuitry 130 performs frequency analysis of velocity information in the reflection wave data received from the transmitting/receiving circuitry 110, extracts blood flow components, tissue components, and contrast agent echo components having been affected by the Doppler effect, and generates data (Doppler data) that is the extraction of moving body information such as velocities, variance, and powers at a plurality of points.

The B-mode processing circuitry 120 and the Doppler processing circuitry 130 illustrated in FIG. 1 can process three-dimensional reflection wave data and two-dimensional reflection wave data. In other words, the B-mode processing circuitry 120 generates two-dimensional B-mode data from the two-dimensional reflection wave data, and generates three-dimensional B-mode data from the three-dimensional reflection wave data. The Doppler processing circuitry 130 generates two-dimensional Doppler data from the two-dimensional reflection wave data, and generates three-dimensional Doppler data from the three-dimensional reflection wave data.

The image generating circuitry 140 generates ultrasound image data from the data generated by the B-mode processing circuitry 120 and the Doppler processing circuitry 130. In other words, the image generating circuitry 140 generates two-dimensional B-mode image data representing the intensities of reflection waves as luminance, from the two-dimensional B-mode data generated by the B-mode processing circuitry 120. In the same manner, the image generating circuitry 140 generates three-dimensional B-mode image data representing the intensities of reflection waves as luminance, from the three-dimensional B-mode data generated by the B-mode processing circuitry 120. The image generating circuitry 140 also generates two-dimensional Doppler image data in which the moving body information is represented, from the two-dimensional Doppler data generated by the Doppler processing circuitry 130. In the same manner, the image generating circuitry 140 generates three-dimensional Doppler image data representing the moving body information from the three-dimensional Doppler data generated by the Doppler processing circuitry 130. The two-dimensional Doppler image data is a velocity image, a variance image, a power image, or an image of a combination thereof. The image generating circuitry 140 can also generate M-mode image data from time-series data of the B-mode data corresponding to one scan line generated by the B-mode processing circuitry 120. The image generating circuitry 140 can also generate a Doppler waveform in which the pieces of velocity information of the blood flow or tissues included in the Doppler data generated by the Doppler processing circuitry 130 are plotted in the temporal order.

At this time, the image generating circuitry 140 generates a piece of ultrasound image data to be displayed, generally by converting a sequence of scan line signals resultant of ultrasound scanning into a sequence of scan line signals in a video format, a typical example of which is that of the television (scan conversion). Specifically, the image generating circuitry 140 generates a piece of ultrasound image data to be displayed by performing coordinate conversion, based on the mode of the ultrasound scanning performed by the ultrasound probe 101. The image generating circuitry 140 also performs various types of image processing other than the scan conversion, such as image processing for re-generating images having averaged luminance, using a plurality of image frames applied with the scan conversion (smoothing process), and image processing in which a differential filter is applied to the image (edge emphasizing process). The image generating circuitry 140 also synthesizes character information indicating various parameters, scales, body marks, and the like to the ultrasound image data.

In other words, the B-mode data and the Doppler data are pieces of ultrasound image data not applied with the scan conversion process, and the data generated by the image generating circuitry 140 is a piece of ultrasound image data to be displayed resultant of the scan conversion process. The B-mode data and the Doppler data are sometimes referred to as raw data. The image generating circuitry 140 generates two-dimensional B-mode image data or two-dimensional Doppler image data that are pieces of two-dimensional ultrasound image data to be displayed, from two-dimensional B-mode data or the two-dimensional Doppler data that are pieces of two-dimensional ultrasound image data not applied with the scan conversion process. The image generating circuitry 140 also generates three-dimensional B-mode image data or three-dimensional Doppler image data that are pieces of three-dimensional ultrasound image data to be displayed from the three-dimensional B-mode data or the three-dimensional Doppler data that are pieces of three-dimensional ultrasound image data not applied with the scan conversion process. Such three-dimensional B-mode image data or three-dimensional Doppler image data are sometimes referred to as volume data that is three-dimensional ultrasound image data.

The image memory 150 is a memory storing therein image data to be displayed, generated by the image generating circuitry 140. The image memory 150 may also store therein data generated by the B-mode processing circuitry 120 and the Doppler processing circuitry 130. The B-mode data and the Doppler data stored in the image memory 150 are enabled to be called by an operator after making a diagnosis, for example, and serve as ultrasound image data to be displayed, via the image generating circuitry 140.

The image generating circuitry 140 stores a piece of ultrasound image data and the time at which ultrasound scanning is performed in order to generate the ultrasound image data in the image memory 150, in a manner mapped to a corresponding ECG received from the electrocardiographic monitor 104. The processing circuitry 170, described later, can acquire the cardiac phase of the time at which the ultrasound scanning is performed in order to generate the corresponding ultrasound image data, by referring to these pieces of data stored in the image memory 150.

The internal storage circuitry 160 stores therein control programs for transmitting and receiving ultrasound, for processing images, and for performing a displaying process, and various types of data such as diagnosis information (such as patient IDs, and observations by physicians), a diagnosis protocol, and various types of body marks. The internal storage circuitry 160 is also used as a storage of the image data stored in the image memory 150, as required. The data stored in the internal storage circuitry 160 can be transferred to an external apparatus via an interface not illustrated. Examples of such an external apparatus include a personal computer (PC) used by a physician making an image diagnosis, a storage medium such as a compact disc (CD) and a digital versatile disc (DVD), and a printer.

The processing circuitry 170 controls the entire processes performed by the ultrasound diagnostic apparatus 1. Specifically, the processing circuitry 170 controls the processes performed by the transmitting/receiving circuitry 110, the B-mode processing circuitry 120, the Doppler processing circuitry 130, and the image generating circuitry 140 based on various types of setting requests entered by an operator via the input device 102, and various control programs and various types of data read from the internal storage circuitry 160. The processing circuitry 170 also controls to display the ultrasound image data to be displayed, stored in the image memory 150 or the internal storage circuitry 160, on the display 103.

The processing circuitry 170 executes an acquiring function 171, a generating function 172, and a display control function 173. Specific processes performed the acquiring function 171, the generating function 172, and the display control function 173 executed by the processing circuitry 170 will be described later.

The processing functions achieved by the acquiring function 171, the generating function 172, and the display control function 173 that are components of the processing circuitry 170 illustrated in FIG. 1 are recorded in the internal storage circuitry 160 as computer-executable programs, for example. The processing circuitry 170 is a processor that implements the functions of the respective computer programs by reading the computer programs from the internal storage circuitry 160, and executing the computer programs. In other words, the processing circuitry 170 having read the computer programs comes to have the functions illustrated inside of the processing circuitry 170 in FIG. 1.

Explained in the embodiment is an example in which the processing functions explained below are implemented by one processing circuit, but the processing circuitry 170 may be implemented as a combination of a plurality of independent processors, and the functions may be implemented by causing the processors to execute the computer programs.

The term "processor" used in the explanation above means a circuit such as a central processing unit (CPU), a graphics processing unit (GPU), an application specific integrated circuit (ASIC), a programmable logic device (such as a simple programmable logic device (SPLD) or a complex programmable logic device (CPLD)), or a field programmable gate array (FPGA). The processor implements a function by reading a corresponding computer program stored in the internal storage circuitry 160, and executing the computer program. The computer program may be embedded directly to the processor circuit, without being stored in the internal storage circuitry 160. In such a configuration, the processor implements a function by reading the corresponding computer program embedded in the circuit, and executing the computer program. Without limitation to a configuration in which each of the processors according to the embodiment is provided as one circuit, the processor may be provided as a combination of a plurality of independent circuits, and the function may be implemented thereby. Furthermore, the components illustrated in the drawings may be integrated into one processor, and the processor may be caused to implement the functions.

The overall configuration of the ultrasound diagnostic apparatus 1 according to the first embodiment is explained above. With such a configuration provided, the ultrasound diagnostic apparatus 1 according to the first embodiment displays a polar-map representing a distribution of local values of a cardiac function index. A Polar-map used in ordinary diagnoses has a display form in which some information related to the regions of interest that are assigned to the surface of the left ventricle is developed onto a two-dimensional plane, with the cardiac apex at the pole. For example, the ultrasound diagnostic apparatus 1 calculates local values of a wall-motion index for the regions of the cardiac left ventricle, as the local function index, and generates a polar-map of the left ventricular local function index, using a left ventricular segment model.

Figure 2A:
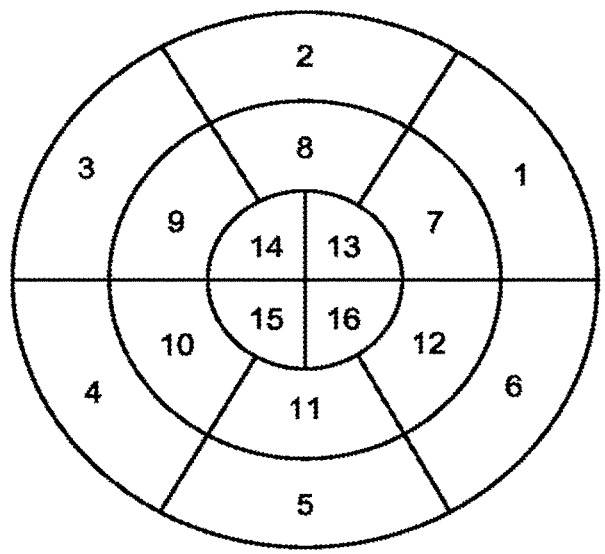
FIG. 2A is a schematic for explaining a process of generating a polar-map of a left ventricle.
Figure 2B:
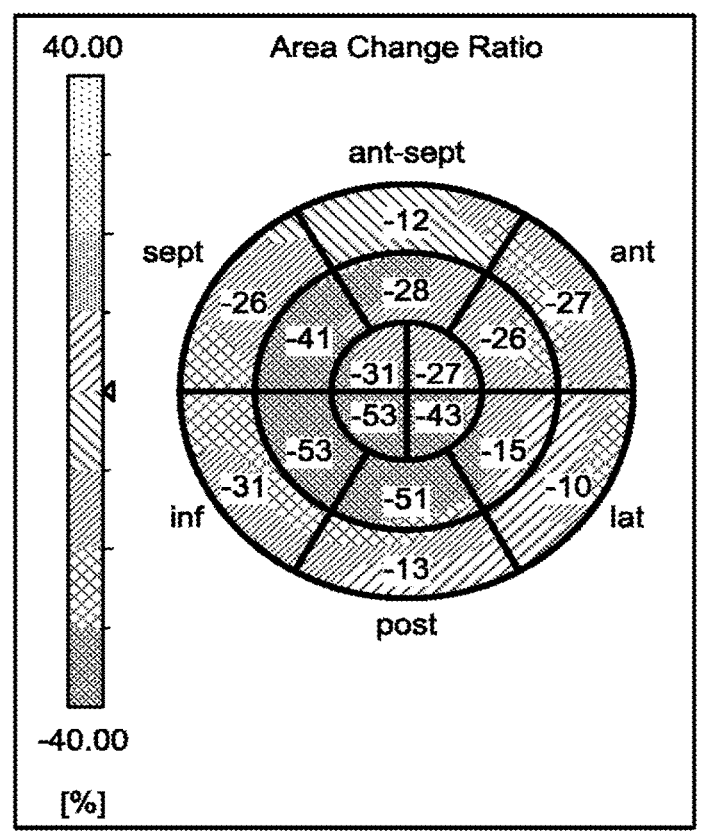
FIG. 2B is another schematic for explaining the process of generating the polar-map of the left ventricle.

For example, FIGS. 2A and 2B are schematics for explaining a generating process of a polar-map of a left ventricle. FIG. 2A illustrates an example of a segment model of a left ventricle. The segment model of a left ventricle is a model diagram in which a left ventricle is developed onto a plane, with the left ventricle divided into 16 local regions (segments), as illustrated in FIG. 2A, for example. FIG. 2B illustrates an example of the polar-map. The ultrasound diagnostic apparatus 1 generates a polar-map by converting the calculated cardiac wall-motion index into a color code, and mapping the color code onto the left ventricular segment model, as illustrated in FIG. 2B.

In the left ventricle, because the mitral valve (blood inlet) and the aortic valve (blood outlet) are located near to each other, and the axes of the directions in which the respective blood flows extend substantially in parallel, there would be practically no problem even if these areas are handled as one open end. Traditionally having been done, in order to measure the volume of the left ventricle, is to close this one open end as an annulus position. The polar-map of the left ventricle has also been acquired by plotting the cardiac apex to the position of the pole, and this one open end to the position of the equator.

Figure 3:
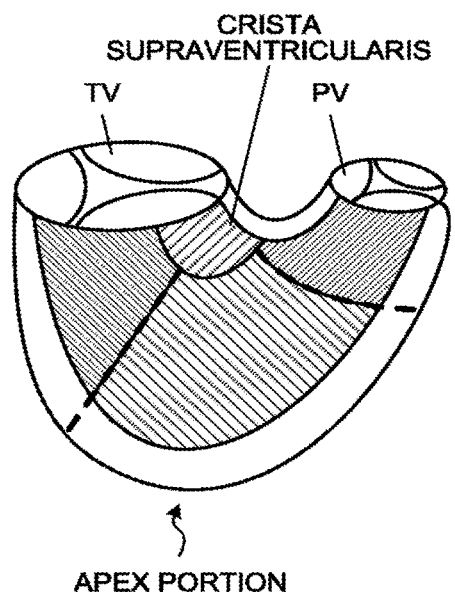
FIG. 3 is a schematic illustrating an example of anatomical regions of a right ventricle.

Some studies for applications of 3DT to the right ventricle (RV) have recently been done, and developments of application programs enabling 3DT to be applied to the right ventricle and having the same functionality as those of the left ventricle have been waited. The positions of anatomical regions of the right ventricle are, however, divided into two, the inlet portion located on the side of the tricuspid valve (TV) (also referred to as an inlet) and the outflow portion located on the side of the pulmonary valve (PV) (also referred to as right ventricle outflow tract (RVOT)), with the crista supraventricularis serving as a connecting portion between the two. The blood flows in these two portions follow the directions with different axes with respect to each other, as illustrated in FIG. 3. In other words, the right ventricle has two open ends with the crista supraventricularis located between the two. Therefore, for the right ventricle, a simple polar-map, such as that of the left ventricle, cannot be acquired by plotting the cardiac apex to the position of the pole. FIG. 3 is a schematic illustrating an example of anatomical regions of a right ventricle. The right ventricle is also referred to as a right chamber.

Figure 4:
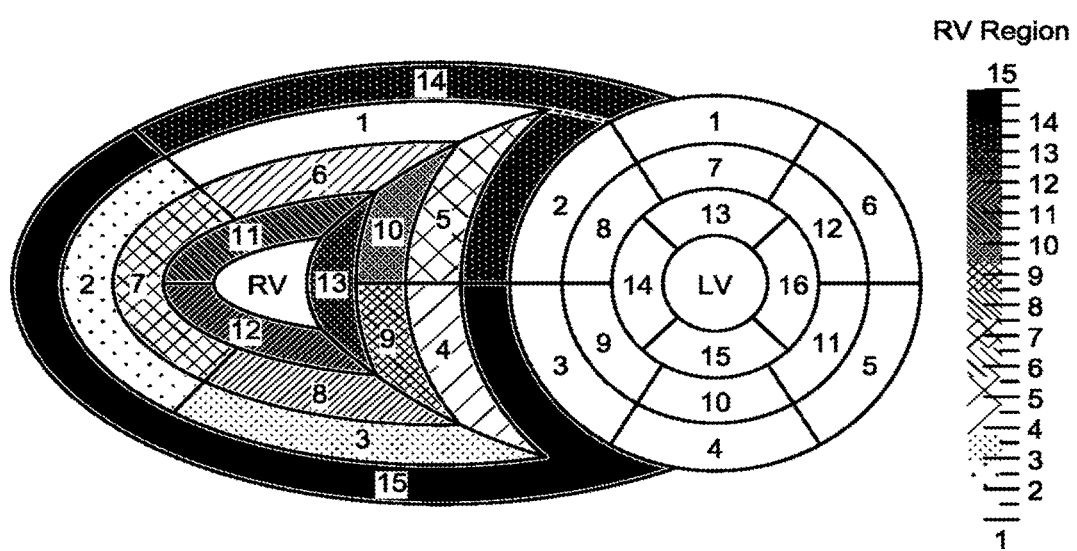
FIG. 4 is a schematic for explaining a conventional example.

The following conventional example of the right ventricular polar-map has been known. FIG. 4 is a schematic for explaining the conventional example. In the example illustrated in FIG. 4, the right ventricular region is mapped to a non-circular image, positioned next to a circular polar-map of the left ventricle. In the example illustrated in FIG. 4, the local region of the right ventricle denoted by the number 14 represents the outflow portion, and the local region of the right ventricle denoted by the number 15 presents the inlet portion. In other words, in the example illustrated in FIG. 4, because the two openings that are separate from each other are connected at two points, their position relation cannot be understood clearly.

Alternatively, by cutting off the right ventricle at a middle level as one open end, instead of at the levels of the annulus regions, and newly creating a conventional circular first polar-map from a viewpoint looking down from the apex, and another (circular) second polar-map with the two openings plotted onto the pole side from the viewpoint looking up from the annulus portions, and by displaying these two polar-maps simultaneously, the positional relation of the crista supraventricularis and the two openings can be expressed in a simple manner in the second polar-map. With this method, however, users are always forced to understand the two polar-maps with different viewpoints, so the user may have trouble understanding the polar-maps.

While a segment model mapped to the region where the coronary artery is dominant has been established as a society-standard for the left ventricle, no standard segment model has been established for the right ventricle. Therefore, intuitive understanding of the positional relation of the right ventricle has not been possible, unlike that achieved by the polar-map of the left ventricle. Executed in the first embodiment to overcome this challenge is a polar-map generating process enabled to provide a single right ventricular polar-map enabling intuitive understanding of the positional relation of the right ventricle. This polar-map generating process is implemented by causing the processing circuitry 170 to execute the acquiring function 171, the generating function 172, and the display control function 173. The acquiring function 171, the generating function 172, and the display control function 173 will now be explained. FIGS. 5 to 11 are schematics for explaining the first embodiment.

The acquiring function 171 acquires a local function index values related to a cardiac right ventricle. For example, the acquiring function 171 calculates local wall-motion index values related to the cardiac right ventricular region from a time series of volume data including the cardiac right ventricular region over a period of at least one cycle, as the local function index values. More specifically, the acquiring function 171 calculates a wall-motion index related to the right ventricular region through a process including frame-by-frame regional pattern matching of volume data included in an acquired group of time series of volume data covering at least one cardiac cycle.

To begin with, the acquiring function 171 sets pieces of identification information for identifying a plurality of respective positions representing a general form of a right ventricle to the corresponding positions in the three-dimensional medical image data. For example, the acquiring function 171 sets a plurality of tracking points, each of which is assigned with an address, to the respective positions representing the contour (surface) of the myocardium of the right ventricle in at least one of the frames of ultrasound image data. A tracking point is a point that is tracked of over some time in order to calculate a wall-motion index of the local region, and is a constitutional point of the contour of the local region. An address is a number assigned to the corresponding tracking point in order to identify such a point, and is defined based on the position of the tracking point on the endocardium, for example. Without limitation to a number, the address may be any identification information such as a character or a symbol capable of identifying the position of a tracking point.

Explained here is an example in which the following process is performed to the endocardium of the right ventricle, but the embodiment is not limited thereto. For example, without limitation to the endocardium, the following process may also be performed to the epicardium or to an intermediate layer between the endocardium and the epicardium. Furthermore, the following process may be performed to any region, such as the left ventricle, the left atrium, the right atrium, or to the entire heart, without limitation to the right ventricle. In the embodiment, the acquiring function 171 sets a plurality of constitutional points making up the contour of the heart, at positions corresponding to the initial contour of the heart, based on the information manually set by the operator. The acquiring function 171 also defines the position of each of such constitutional points in the endocardium as P_endo (t, h, d).

The acquiring function 171 keeps track of the positions of the constitutional points across a plurality of frames of ultrasound image data included in the group of time series of ultrasound image data, by performing a process including pattern matching using the ultrasound image data having been set with the constitutional points, and another frame of ultrasound image data.

For example, once a plurality of constitutional points are set to the positions corresponding to the initial contour in the volume data in a frame t=0 included in the group of volume data frames, the acquiring function 171 keeps track of the positions of the constitutional points in another frame t, through the process including pattern matching. Specifically, the acquiring function 171 performs pattern matching repeatedly between the volume data the frame for which the constitutional points have been set and another piece of volume data in a frame adjacent to such a frame. In other words, the acquiring function 171 keeps track of the positions of the respective constitutional points P_endo (t, h, d) included in the volume data in each of the frames t=1, 2, 3 . . . , using the constitutional points of the endocardium P_endo (0, h, d) in the volume data at t=0 as starting points. As a result, the acquiring function 171, acquires the coordinate information of each of the constitutional points plotted on the endocardium, for each of the frames included in an interval corresponding to one heartbeat.

The acquiring function 171 then calculates a wall-motion index representing a motion of tissues, for each of a plurality of Nieces of ultrasound image data, using the positions of the respective constitutional points in a plurality of pieces of ultrasound image data included in each group of pieces of ultrasound image data.

Representative examples of the wall-motion index calculated by the acquiring function 171 include a local myocardial displacement [mm] at each constitutional point in increments of one frame, a local myocardial strain [%] that is the ratio of a change in the distance between two points in a predetermined direction, and a local myocardial velocity [cm/s] and a local myocardial strain rate [1/s] that are temporal changes of the local myocardial strain and the local myocardial velocity, respectively. Actual examples of the predetermined direction include longitudinal strain in the longitudinal direction and circumferential strain in the circumferential direction. Furthermore, information referred to as dyssynchrony imaging (DI) may also be calculated by using these wall-motion indices as inputs and outputting a peak timing (time) of the index values. In the three-dimensional speckle tracking, an area change ratio (AC) of a boundary surface can also be calculated.

The wall-motion index calculated by the acquiring function 171 is assigned to each of the constitutional points (tracking points) having been used in the calculation. Specifically, for example, the wall-motion index calculated from each of the constitutional points of the endocardium is defined as V_endo (t, h, d). The acquiring function 171 then stores the calculated wall-motion index in the image memory 150, for each group of volume data pieces. In the manner described above, the acquiring function 171 calculates the local wall-motion index values through a process including a local tracking process.

The generating function 172 generates a three-dimensional image based on the local function index values. For example, the generating function 172 generates a three-dimensional image of the right ventricle through a surface rendering (SR) process (hereinafter, referred to as an SR image). An SR image is an image in which the three-dimensional image generated using the volume data of the right ventricle is divided into a plurality of regions of interest, with the wall-motion index assigned to each of the regions of interest, for example.

The generating function 172 also generates a right ventricular polar-map, representing a distribution of the local function index values using a right ventricular segment model. The segment model provides a model diagram in which the right ventricle is developed onto a plane, and the inlet portion leading blood into the right ventricle and the outflow portion leading the blood out from the right ventricle are positioned separately from each other on the external circumference of the model diagram. Each position in this right ventricular polar-map is mapped to the corresponding position in the SR image through a predetermined coordinate conversion.

At this time, the generating function 172 generates a right ventricular polar-map satisfying, for example, the four conditions listed below. In other words, a condition (1) is to have the two openings that are those of the inlet portion (tricuspid valve) and the outflow portion (pulmonary valve) dissected and plotted to the circumferential edge of the polar-map. The condition (2) is to have the cardiac apex potted to the pole, and to have the areas that are hidden and invisible in a view from the side of the cardiac apex (three regions of the circumference of the inlet portion, the circumference of the outflow portion, and the crista supraventricularis) developed onto and presented in the dissected portions. The condition (3) is to have the edges that are connected to each other (at three positions including those on the circumference of the inlet portion, the circumference of the outflow portion, and the crista supraventricularis) share the same position as their inputs. The condition (4) is to present the edges that are connected to each other (at the three positions including those on the circumference of the inlet portion, the circumference of the outflow portion, and the crista supraventricularis) as being connected to each other.

Among the conditions (1) to (4), the condition (1) is a mandatory condition, and the conditions (2) to (4) are conditions that can be selected as appropriate. Therefore, the generating function 172 generates a right ventricular polar-map at least satisfying the condition (1). For example, the generating function 172 may generate a right ventricular polar-map satisfying only the condition (1), or generate a right ventricular polar-map satisfying the conditions (1) to (4). In other words, the generating function 172 generates a right ventricular polar-map satisfying any combination of the conditions (2) to (4), in addition to the condition (1).

In the explanation hereunder, a right ventricular segment model will be explained to begin with, and the polar-map generating process will then be explained. The right ventricular segment model is also referred to as a medical model diagram of the right ventricle, and the right ventricular polar-map is also referred to as a functional image of the right ventricle.

Figure 5A:
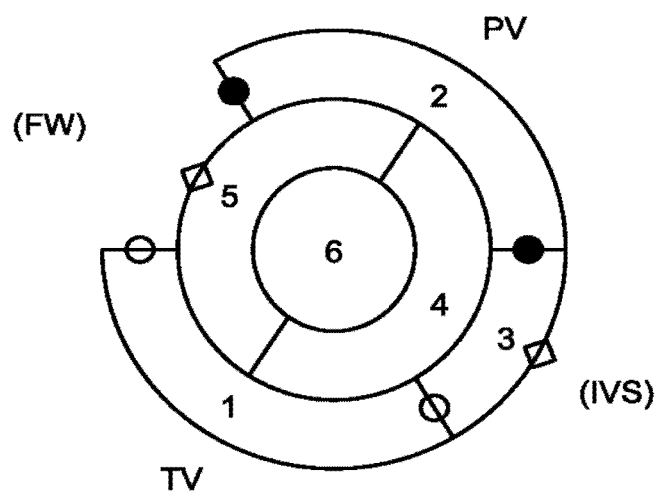
FIG. 5A is another schematic for explaining the first embodiment.
Figure 5B:
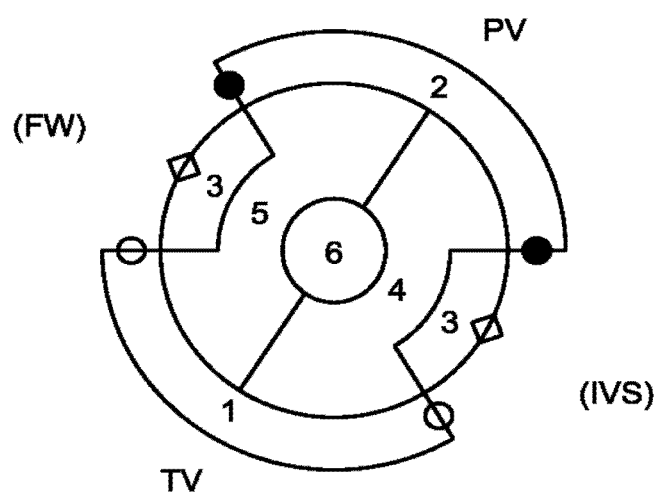
FIG. 5B is another schematic for explaining the first embodiment.

FIGS. 5A to 5C illustrate right ventricular segment models. The right ventricular segment model illustrated in each of FIGS. 5A to 5C provides a model diagram in which the right ventricle is developed onto a plane, is a medical model diagram of a right ventricle in which the region separating the inlet portion and the outflow portion is dissected, and the inlet portion and the outflow portion are plotted at positions that are separated from each other. The right ventricular segment model illustrated in FIGS. 5A and 5B present the positional relation between the two openings of the right ventricle and the crista supraventricularis extending between the two openings in an intuitively understandable manner.

More specifically, the right ventricular segment model illustrated in FIG. 5A is a model diagram of the right ventricle divided into six local regions (segments), and with the inlet portion (TV) plotted to the local area denoted by the number 1, and with the outflow portion (PV) plotted to the local area denoted by the number 2. In the right ventricular segment model illustrated in FIG. 5A, the crista supraventricularis is plotted to the local area denoted by the number 3, near the interventricular septum (IVS). In the right ventricular segment model illustrated in FIG. 5A, the apex portions are plotted to the local areas denoted by the number 4 to the number 6. An apex portion on the side of the interventricular septum is plotted to the local area denoted by the number 4, and an apex portion on the side of the free wall (FW) is plotted to the local area denoted by the number 5. The apex is plotted to the local area denoted by the number 6.

The right ventricular segment model illustrated in FIG. 5B is a model diagram of the right ventricle divided into six local regions (segments), with the inlet portion (TV) plotted to the local area denoted by the number 1, and with the outflow portion (PV) plotted to the local area denoted by the number 2. In the right ventricular segment model illustrated in FIG. 5B, the crista supraventricularis is plotted to the local areas denoted by the numbers 3 that are separate areas on the side of interventricular septum and on the side of the free wall. In the right ventricular segment model illustrated in FIG. 5B, the apex portions are plotted to the local areas denoted by the number 4 to the number 6. At this time, the apex portion on the side of the interventricular septum is plotted to the local area denoted by the number 4, and the apex portion on the side of the free wall is plotted to the local area denoted by the number 5. The apex is plotted to the local area denoted by the number 6.

The right ventricular segment model illustrated in FIG. 5C represents the positional relation of the two openings in the right ventricle in an intuitively understandable manner. The right ventricular segment model illustrated in FIG. 5C is a model diagram of the right ventricle divided into seven local regions (segments). Explicitly shown in the right ventricular segment model illustrated in FIG. 5C are a PV-side hinge 21 connecting the right ventricular wall and the left ventricular wall, and a TV-side hinge 22. The PV-side hinge 21 explicitly divides the RVOT into the areas on the side of the interventricular septum (area denoted by the number 4) and the side of the free wall (the area denoted by the number 5), and the TV-side hinge 22 explicitly divides the inlet portion into the areas on the side of the free wall (the area denoted by the number 2) and the side of the interventricular septum (the area denoted by the number 3). In the right ventricular segment model illustrated in FIG. 5C, the blood inlet on the lateral side of the free wall is plotted to the local area denoted by the number 1, and the inlet portion on the inferior side of the free wall is plotted to the local area denoted by the number 2. The apex portions are then plotted to the local areas denoted by the number 6 and the number 7. The apex portion on the side of the free-wall is plotted to the local area denoted by the number 6, and the apex portion on the side of the interventricular septum is plotted to the local area denoted by the number 7.

The right ventricular segment models illustrated in FIGS. 5A to 5C can identify the corresponding positions having been at the same position before the region separating the inlet portion and the outflow portion is dissected. For example, white circle markers represent the corresponding positions having been at the same position before the region is dissected, and black circle markers represent corresponding positions having been at the same position before the region is dissected. The diamond markers also represent the corresponding positions having been at the same position before the region is dissected.

Figure 6A:
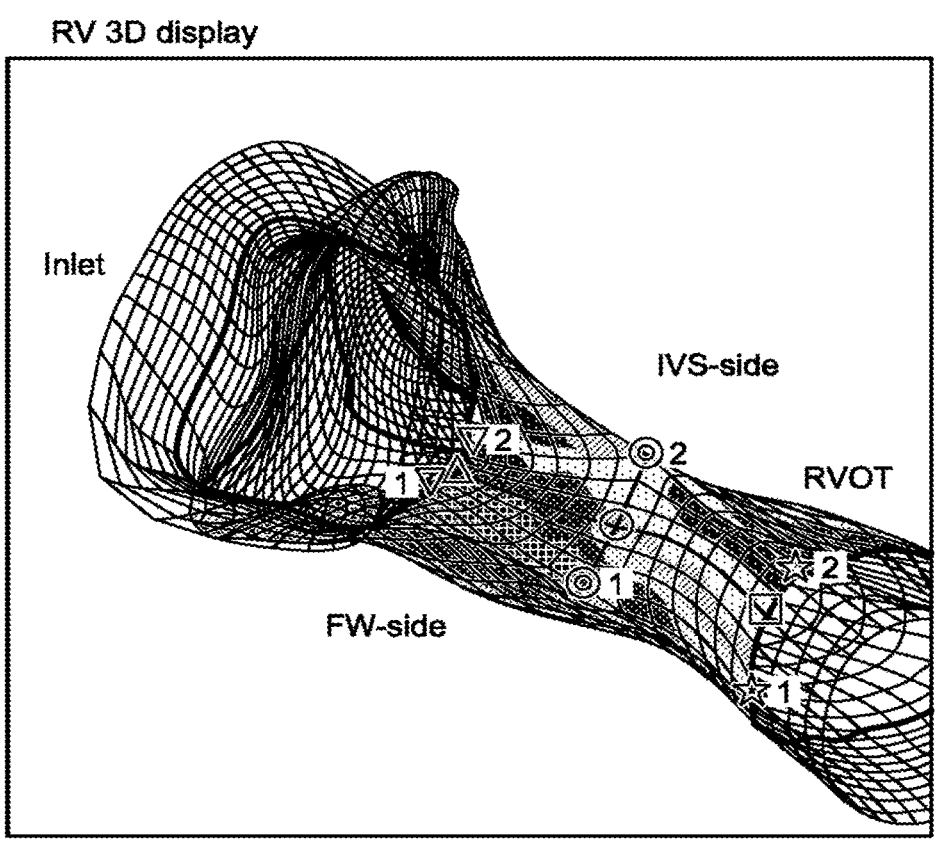
FIG. 6A is another schematic for explaining the first embodiment.

A generating process of the right ventricular polar-map will now be explained. FIG. 6A illustrates an SR image of the right ventricle. The SR image illustrated in FIG. 6A is a three-dimensional image that is based on the local function index values. The SR image illustrated in FIG. 6A is a model diagram presenting the right ventricle in a view from a direction looking up from the side of the inlet portion and the outflow portion. To perceive the inlet portion and the outflow portion in the SR image metaphorically as a pair of trousers, the part corresponding to the crotch appended with a white circle marker corresponds to the crista supraventricularis. The inseam on the left leg of the trousers appended with a triangle marker corresponds to the inside of the inlet portion, and the inseam on the right leg of the trousers appended with a square marker corresponds to the inside of the outflow portion. These areas are regions that will be hidden when the SR image is looked down upon from the side of the apex. In other words, when the SR image is looked down from the side of the apex, the user is incapable of observing the inlet portion, the outflow portion, and the crista supraventricularis, directly.

Figure 6B:
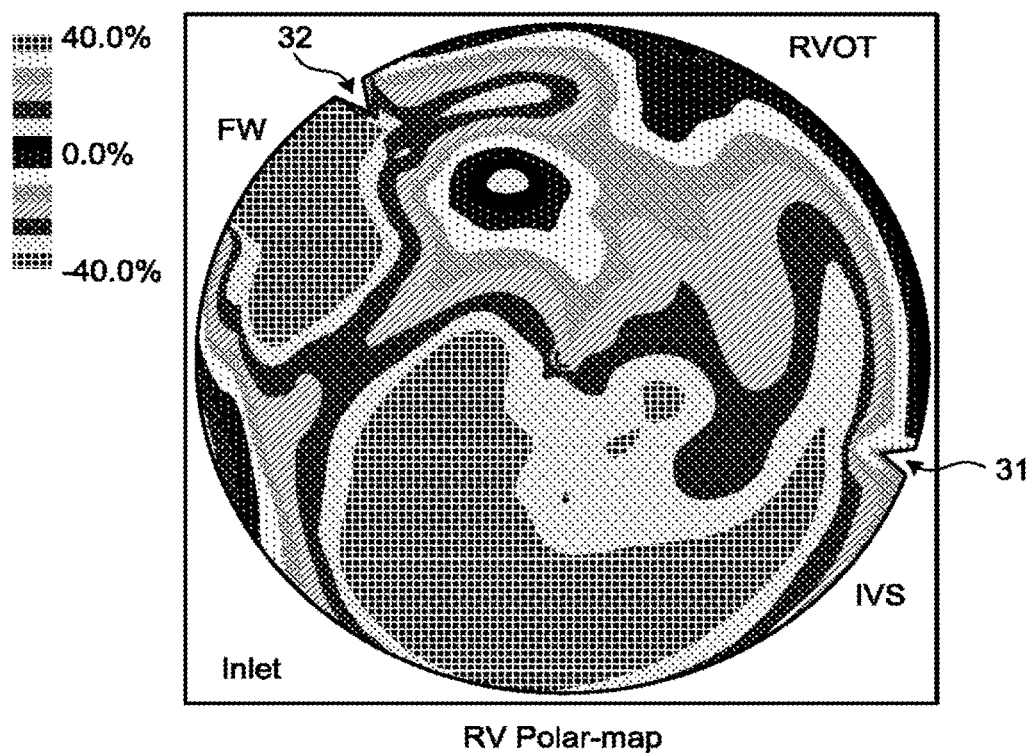
FIG. 6B is another schematic for explaining the first embodiment.

Therefore, the generating function 172 according to the first embodiment generates a right ventricular polar-map such as that illustrated in FIG. 6B, by dissecting the SR image across the line connecting the triangle, the circle, and the square markers, and by developing the image onto the right ventricular segment model. At this time, each position in the right ventricular polar-map is mapped to the corresponding position in the SR image, through a predetermined coordinate conversion. In other words, the generating function 172 generates a right ventricular polar-map in which a function index value of the position corresponding to the region separating the inlet portion and the outflow portion is mapped to the corresponding region in the right ventricular segment model.

In FIG. 6A, a reversed triangle marker 2, a double circle marker 2, and a star marker 2 point the side of the interventricular septum (IVS), and a reversed triangle marker 1, a double circle marker 1, and a star marker 1 point the side of the free wall (FW). The region surrounded by the reversed triangle marker 2, the double circle marker 2, the star marker 2, and the triangle marker, the circle marker, and the square marker is mapped to a dissected area 31 at the position of three and a half o'clock in the polar-map illustrated in FIG. 6B, and the region surrounded by the reversed triangle marker 1, the double circle marker 1, and the star marker 1, and the triangle marker, the circle marker, and the square marker corresponds to a dissected area 32 at the position of ten and a half o'clock in the polar-map illustrated in FIG. 6B.

The region that will be hidden in the view from a direction looking down on the SR image from the side of the apex is mapped as V-shaped regions having some width in the respective dissected areas in the polar-map. During this mapping, because the area corresponding to the line connecting the triangle, the circle, and the square markers is mapped to the same position in both of the dissected areas, the dissected areas share the same position, as the input wall-motion index value. In other words, using a medical model diagram of the right ventricle in which the region separating the inlet portion and the outflow portion is dissected, and the inlet portion and the outflow portion plotted to positions that are separated from each other, the generating function 172 generates a functional image of the right ventricle by assigning the same function index value to the corresponding positions having been at the same position before the region is dissected.

Figure 6C:
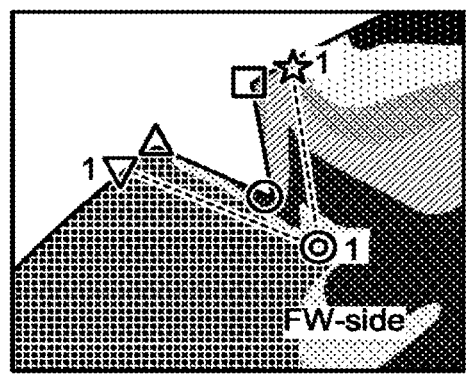
FIG. 6C is another schematic for explaining the first embodiment.
Figure 6D:
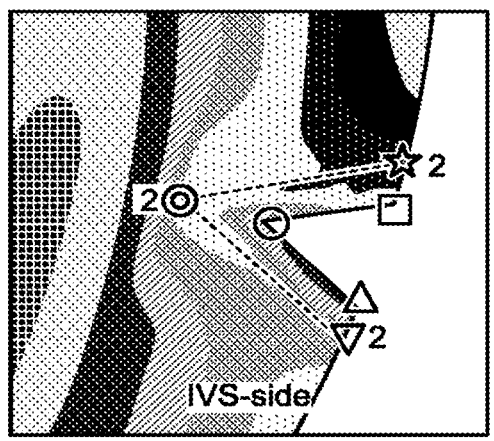
FIG. 6D is another schematic for explaining the first embodiment.

FIG. 6C is an enlarged view of the dissected area 32, and FIG. 6D is an enlarged view of the dissected area 31. The markers appended to the SR image illustrated in FIG. 6A are superimposed in FIGS. 6C and 6D. In this example, the triangle marker, the circle marker, and the square marker illustrated in FIG. 6C, and the triangle marker, the circle marker, and the square marker illustrated in FIG. 6D correspond to the triangle marker, the circle marker, the square marker illustrated in FIG. 6A. In other words, the triangle marker, the circle marker, the square marker indicate that those illustrated in FIG. 6C and those illustrated in FIG. 6D are at the same positions. In the manner described above, the generating function 172 generates a functional image of the right ventricle appended with information for identifying the corresponding positions having been at the same position before the region separating the inlet portion and the outflow portion is dissected. By superimposing such markers over the polar-map, the user can understand that the regions divided and developed are mapped to each other, that the inlet portion and the outflow portion are divided in the circumferential direction, and these areas are connected to each other in the circumferential direction, intuitively.

Figure 7A:
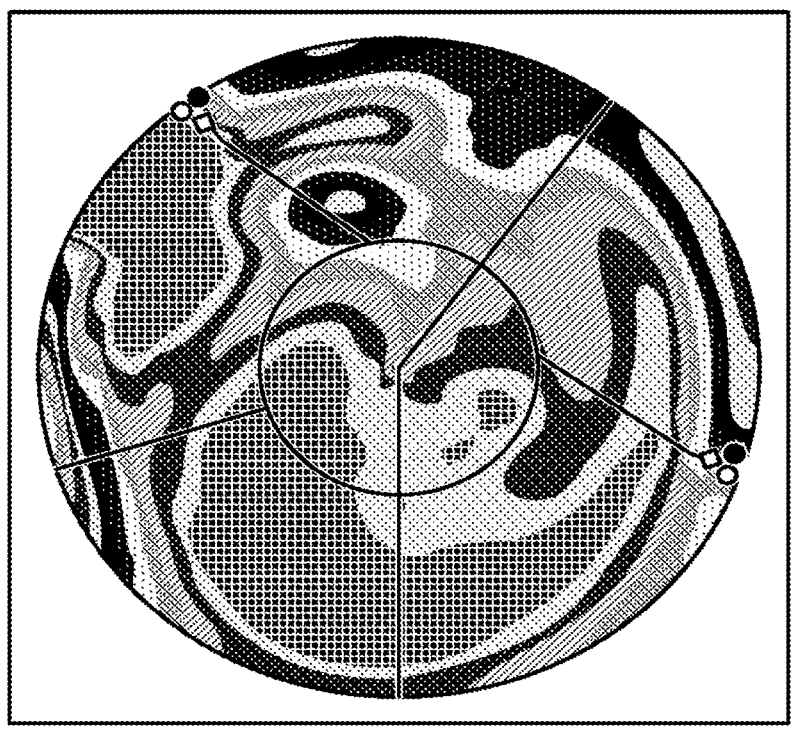
FIG. 7A is another schematic for explaining the first embodiment.
Figure 7B:
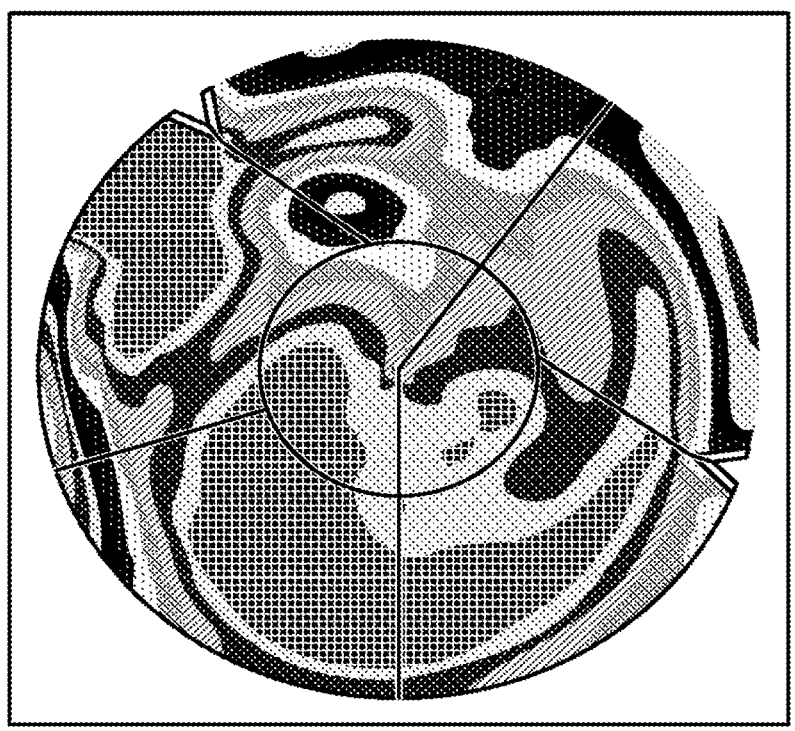
FIG. 7B is another schematic for explaining the first embodiment.

To explain with an example, the generating function 172 generates a right ventricular polar-map illustrated in FIG. 7A or 7B. Explained with the example illustrated in FIGS. 7A and 7B is an example in which a right ventricular polar-map is generated using a segment model illustrated in FIG. 5C. The right ventricular polar-map is divided into a plurality of regions of interest by border lines. The border lines for dividing the right ventricular polar-map are also referred to as first border lines. Illustrated in the example in FIGS. 7A and 7B are the position of borders that divide the right ventricular polar-map into a plurality of regions of interest in the right ventricular polar-map.

For example, the right ventricular polar-map illustrated in FIG. 7A is an example in which all of the conditions (1) to (4) are satisfied. In other words, in the right ventricular polar-map illustrated in FIG. 7A, the two openings on the side of the inlet portion (tricuspid valve) and on the side of the outflow portion (pulmonary valve) are dissected and plotted onto the edge of the circumference of the polar-map. The right ventricular polar-map illustrated in FIG. 7A positions the cardiac apex at the pole, and presents the regions that are hidden and invisible from the side of the cardiac apex (three regions including the circumference of the inlet portion, the circumference of the outflow portion, and crista supraventricularis) in a manner developed onto the separate portions. Furthermore, in the right ventricular polar-map illustrated in FIG. 7A, the edges that re connected to each other (three positions including those on the circumference of the inlet portion, the circumference of the outflow portion, and the crista supraventricularis) share the same positions as inputs.

The generating function 172 superimposes the white circle markers, the black circle markers, and the diamond markers over the right ventricular polar-map, at the positions corresponding to the inlet portion, the outflow portion, and the crista supraventricularis, respectively. In the exemplary visual representation illustrated in FIG. 7A, the white circle markers connect the inlet portion, the black circle markers connect the outflow portion, and the diamond markers connect the crista supraventricularis, representing that these positions that are mapped to each other share the same inputs.

The right ventricular polar-map illustrated in FIG. 7B is an example in which only the condition (1) is satisfied. As an example, FIG. 7B illustrates an example in which only mapped are the regions not hidden in a view from the cardiac apex, without mapping the regions hidden in such a view. In such an example, because there are no areas that are connected to each other, it is not necessary to show the connection markers in the polar map. Even in an example such as that illustrated in FIG. 7B, users can easily understand that the inlet portion and outflow portion are dissected at the position of the V-shaped cut.

Figure 8:
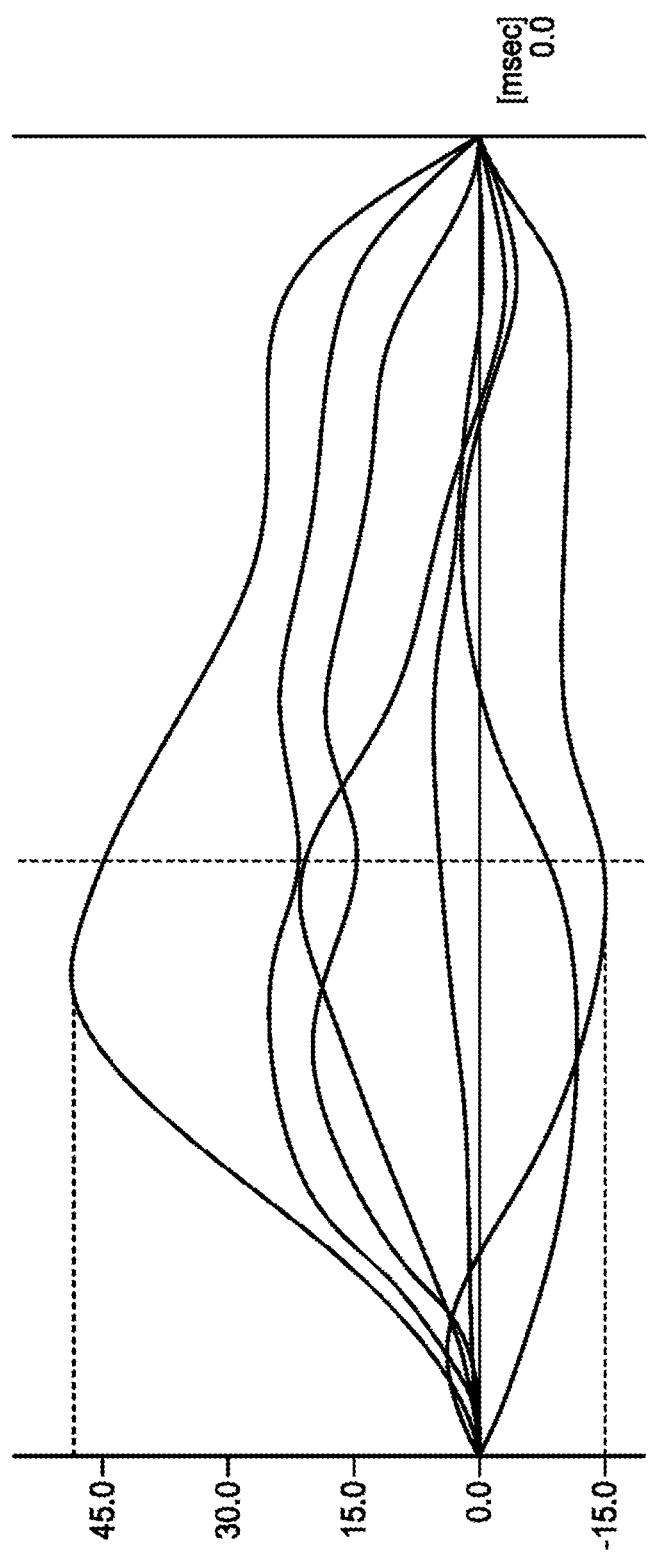
FIG. 8 is another schematic for explaining the first embodiment.

The generating function 172 also divides the right ventricular region into a plurality of regions of interest, and generates a curve representing a temporal change in the value of the wall-motion index related to each of such regions of interest. In FIG. 8, the horizontal axis represents time, and the vertical axis represents wall-motion index values. The generating function 172 generates, for example, a curve representing a temporal change in a representative value of the wall-motion information in each of the local regions, as illustrated in FIG. 8. The representative value of the wall-motion information may be the average of the wall-motion information values, or the maximum or the minimum value of the wall-motion information, for example. In a configuration in which the generating function 172 does not map the hidden region, as in the example illustrated in FIG. 7B, it is preferable to exclude the portion having been excluded from the mapping (e.g., the region numbered 1, 3, 4, and 5 in the right ventricular segment model illustrated in FIG. 5C) from the calculation of the representative values of the respective local regions.

The display control function 173 causes the display 103 to display the functional image of the right ventricle. For example, the display control function 173 causes the display 103 to display the right ventricular polar-map illustrated in FIG. 7A or 7B.

Figure 9:
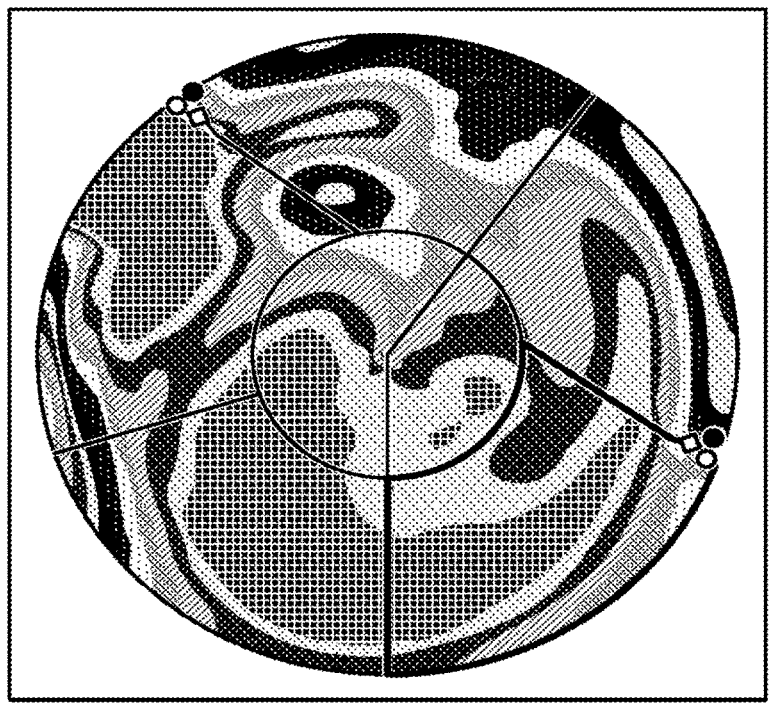
FIG. 9 is another schematic for explaining the first embodiment.

The display control function 173 displays the border positions at which the functional image of the right ventricle is divided into a plurality of regions of interest, in the functional image of the right ventricle, and changes the display state of the border position depending on whether the corresponding region of interest is selected or not selected. FIG. 9 illustrates an example in which the local area denoted by the number 3 in FIG. 5C (the region corresponding to the inlet portion on the side of the interventricular septum) is selected. The display control function 173 then highlights, for example, the border line around the region corresponding to the selected inlet portion on the side of the interventricular septum, as illustrated in FIG. 9, on the display 103. The display control function 173 may also delete the border lines around the regions of interest other than the selected region of interest.

Figure 10:
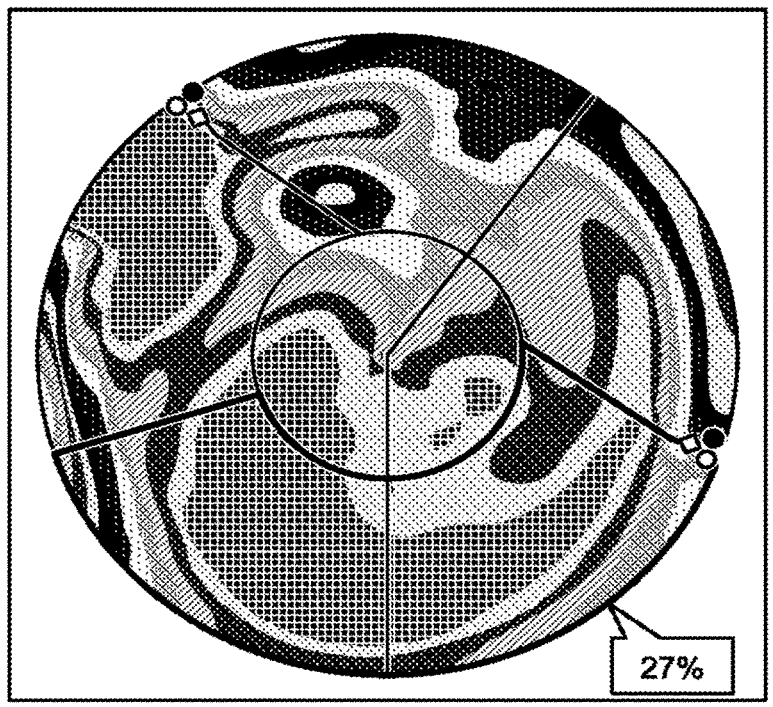
FIG. 10 is another schematic for explaining the first embodiment.

The display control function 173 also causes the display 103 to display the function index value related to the region of interest that is selected in the functional image of the right ventricle. FIG. 10 illustrates an example in which the local area denoted by the number 3 in FIG. 5C (the region corresponding to the inlet portion on the side of the interventricular septum) and the local area denoted by the number 2 in FIG. 5C (the region corresponding to the inlet portion on the inferior side of the free wall) are selected. For example, the display control function 173 calculates a representative value of the function index corresponding to the selected regions of interest, and causes the display 103 to display the representative value, as illustrated in FIG. 10. In the example illustrated in FIG. 10, the average of the function index values across the regions corresponding to the inlet portions on the side of the interventricular septum and on the inferior side of the free wall is "27%". The display control function 173 may cause the display 103 to display the function index value in each of the selected region of interest, or cause the display 103 to display the sum of the function index values by calculating the sum across the entire selected regions of interest.

The display control function 173 also causes the display 103 to display the curves of the temporal change for the respective regions. At this time, it is preferable to present the line representing the temporal change curve corresponding to the selected region of interest in a manner distinguishable from those corresponding to the other regions of interest. In such a configuration, upon receiving a selection of an area corresponding to any one of the regions of interest in the functional image of the right ventricle, or upon receiving a selection of the temporal change curve corresponding to any one of the regions of interest, the display control function 173 displays the area of the functional image of the right ventricle and the curve representing the temporal change corresponding to the selected region of interest in a display form different from that used for areas of the functional image of the right ventricle and curves representing temporal changes corresponding to unselected region of interests.

An example will now be explained with reference to FIG. 11. FIG. 11 illustrates an example in which the right ventricular polar-map is displayed on the left side of the display 103, and the curves of the temporal changes are displayed on the right side of the display 103. When a selection of one of the temporal change curves is received from a user making an operation of a cursor 41, the display control function 173 causes the display 103 to highlight the selected temporal change curve and the border line around the area corresponding to the selected region of interest in the right ventricular polar-map. FIG. 11 illustrates an example in which the temporal change curve corresponding to the local area denoted by the number 3 in FIG. 5C (the region corresponding to the inlet portion on the side of the interventricular septum) is selected. The display control function 173 may not show the temporal change curves and the areas corresponding to the regions of interest other than the selected one, the right ventricular polar-map.

A process performed by the ultrasound diagnostic apparatus 1 according to the first embodiment will now be explained with reference to FIG. 12. FIG. 12 is a flowchart illustrating a process performed by the ultrasound diagnostic apparatus 1 according to the first embodiment. FIG. 12 illustrates a flowchart for explaining the entire operation performed by the ultrasound diagnostic apparatus 1, and explained now is which functional unit corresponds to which step in the flowchart.

Steps S1 to S2 are steps corresponding to the acquiring function 171. These are steps at which the acquiring function 171 is implemented by causing the processing circuitry 170 to call a predetermined computer program corresponding to the acquiring function 171 from the internal storage circuitry 160, and executing the predetermined computer program. At Step S1, the acquiring function 171 acquires a piece of volume data including the image of the right ventricle over a period of at least one cycle. For example, the acquiring function 171 acquires the volume data generated by the image generating circuitry 140 from the image memory 150.

At Step S2, the acquiring function 171 calculates a wall-motion index. For example, the acquiring function 171 calculates a local wall-motion index value through the speckle tracking process. As the wall-motion index value, the acquiring function 171 calculates any of strain, the ratio of area change, displacement, the ratio of change in the strain over time, the ratio of change in the ratio of area change over time, and the ratio of displacement change over time.

Steps S3 to S5 are steps corresponding to the generating function 172. These are steps at which the generating function 172 is implemented by causing the processing circuitry 170 to call a predetermined computer program corresponding to the generating function 172 from the internal storage circuitry 160 and to execute the predetermined computer program. At Step S3, the generating function 172 generates an SR image. For example, the generating function 172 generates an SR image such as that illustrated in FIG. 6A.

At Step S4, the generating function 172 generates a right ventricular polar-map. For example, the generating function 172 generates a right ventricular polar-map such as those illustrated in FIGS. 7A and 7B. At Step S5, the generating function 172 generates the curves representing the temporal change. For example, the generating function 172 generates the temporal change curves such as those illustrated in FIG. 8.

Step S6 is a step corresponding to the display control function 173. This is a step at which the display control function 173 is implemented by causing the processing circuitry 170 to call a predetermined computer program corresponding to the display control function 173 from the internal storage circuitry 160 and to execute the predetermined computer program. At Step S6, the display control function 173 causes the display 103 to display the SR image, the right ventricular polar-map, and the temporal change curves.

As described above, in the first embodiment, new layout-related conditions (1) to (4) are applied to various right ventricular segment models. Therefore, according to the first embodiment, it is possible to generate a polar-map enabling the positional relation of the right ventricle to be easily recognized. Even if some society organization, such as the ASE or the AHA, enacts a right ventricular segment model, the embodiment described above can be applied to the enacted right ventricular segment model.

Furthermore, in the first embodiment, various types of functions having been known in the left ventricle 3DT according to conventional examples (such as highlighting and switching of selected/not-selected state) can be applied to a plurality of local regions of interest that are illustrated as numbered in the right ventricular segment model. Therefore, in the first embodiment, a curve representing a temporal change in a myocardial strain, for example, corresponding each segment in an RV-3DT application program can be controlled using a polar-map of right ventricle. As a result, according to the first embodiment, it becomes possible to provide an RV-3DT application program with the same operability and the same functions as those of the LV-3DT application programs with which users of LV polar-maps are already familiar.

Modification of First Embodiment

Explained in the embodiment described above is an example in which a right ventricular polar-map is generated by dissecting the region separating the inlet portion and the outflow portion within the SR image of the right ventricle, and developing the right ventricle onto a right ventricular segment model. There are some situations in which there are some changes in the positions of the borders involving a plurality of local areas in the SR image. To address this issue, explained in a modification of the first embodiment is an example in which the right ventricular polar-map is changed as the border positions are changed in the SR image. The border lines dividing the image are sometimes referred to as second border lines.

The display control function 173 receives a change in the positions of the second border lines dividing the SR image into a plurality of regions of interest. For example, when such a border line is designated with a mouse cursor, the display control function 173 receives such an operation as a designation of a border line to be changed.

The display control function 173 then receives designations of the direction and the amount of movement. The display control function 173 then changes the position of the border line based on the instruction of the change. At this time, the display control function 173 changes the border line based on the positions each of which is assigned with an address (constitutional point). For example, the vertexes at both ends of the border line to be changed are denoted as a vertex A and a vertex B, respectively. Explained here is an example in which the position of the vertex A is (h1, d1), the position of the vertex B is (h2, d2), and the direction of movement is to the left, and the amount of movement is "a". In this example, the display control function 173 moves the vertex A and the vertex B toward the left by "a". In other words, the display control function 173 adds "a" to the position of the vertex A in the circumferential direction as (h1, d1+a). The display control function 173 also adds "a" to the position of the vertex B in the circumferential direction as (h2, d2+a) in the same manner. The display control function 173 then draw a border line connecting the vertex A and the vertex B having been applied with the change. As a result, the border line is moved to the left.

The display control function 173 controls in such a manner that any change in the position of a second border line does not cause in any discontinuity to any of the borders in the right ventricular polar-map. For example, before receiving a change in the position of the second border line on the SR image, the display control function 173 establishes some setting for making any discontinuity resulting from such a change to be unnoticeable, in relation to the corresponding border position in the right ventricular polar-map. In other words, when a change in the position of the second border line is to be received, and some change in the right ventricular polar-map is to be applied, the display control function 173 restricts accepting a change in the position of the second border line at a position where the first border lines intersect with each other.

For example, the positions corresponding to the areas around the circumferential edge of the right ventricular polar-map are suitable, as the areas where any change in the position of a second border line is permitted. In other words, because any area outside of the area to be included in the image will not be shown, no unnatural visible discontinuity will be introduced even if the position of border corresponding to an area around the circumferential edge is changed in the radial direction. Some specific examples in which no unnatural discontinuity is introduced will now be explained with reference to FIGS. 13A and 13B.

Figure 13A:
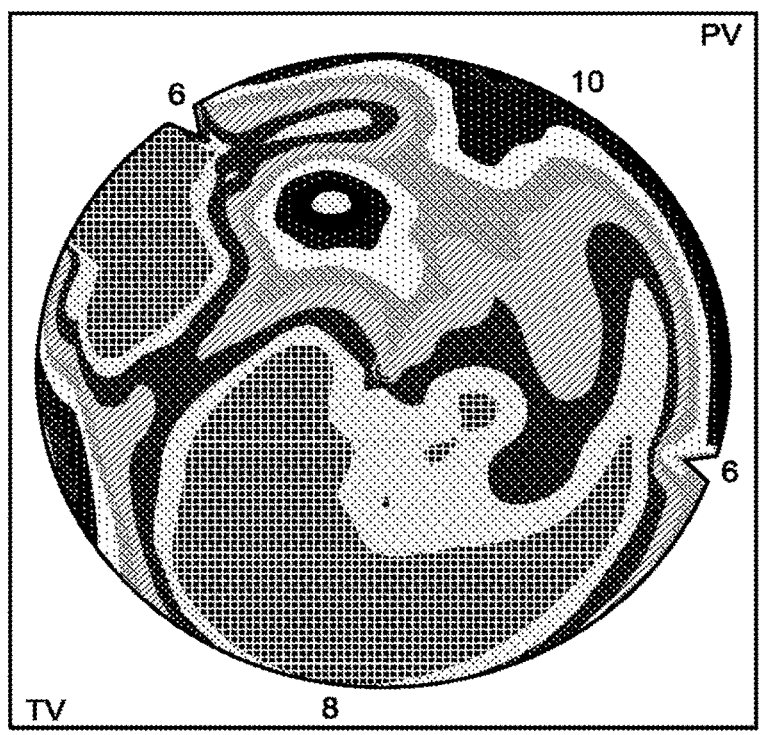
FIG. 13A is a schematic, for explaining a modification of the first embodiment.
Figure 13B:
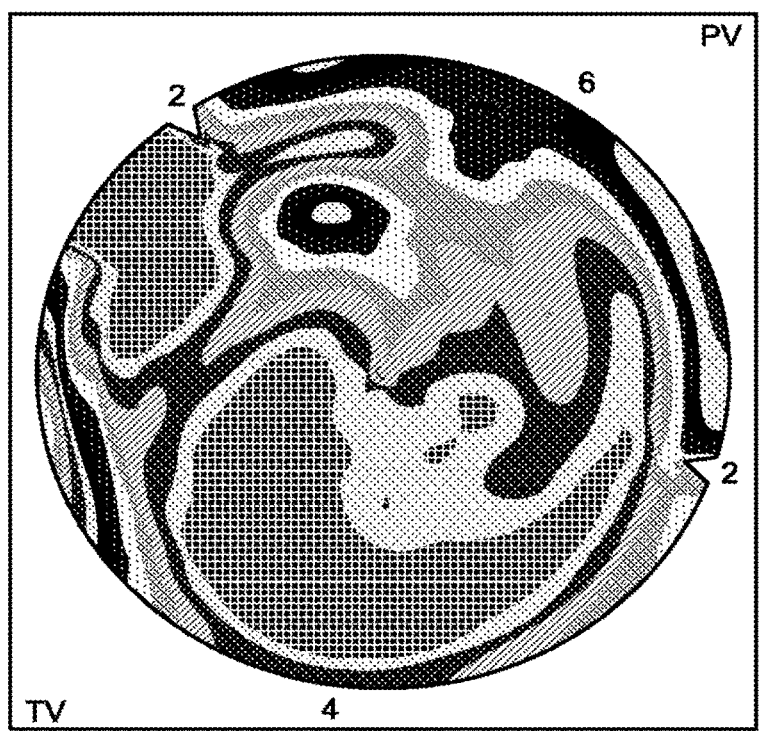
FIG. 13B is another schematic for explaining the modification of the first embodiment.

FIGS. 13A and 13B illustrate examples of a right ventricular polar-map in which the level of the TV edge, corresponding to the position of the annulus of the tricuspid valve, and the level of the PV edge, corresponding to the position of the annulus of the pulmonary valve, are changed in the vertical direction. Each number in FIGS. 13A and 13B represents the level of the edge of the corresponding area. The TV edge and the PV edge are both at higher levels nearer to the cardiac apex) in FIG. 13A, and the TV edge and the PV edge are both at lower levels (further away from the cardiac apex) in FIG. 13B. The edge level is changed by four in increments of an address, between FIG. 13A and FIG. 13B. In FIG. 13A, looking at the circumferential edge of the right ventricular polar-map, the regions at a level near and shallower with respect to the cardiac apex are represented enlarged in the radial direction, in a view from the apex side. More specifically, the mapping information of the regions around the edge in FIG. 13B at deeper levels are not represented in FIG. 13A. By contrast, in FIG. 13B, looking at the circumferential edge of the right ventricular polar-map, the TV edge and the PV edge are set to the lower levels (further away from the cardiac apex), so that the regions at levels further away from to the apex and deeper with respect to the apex is represented as compressed in the radial direction, in a view from the apex side.

An example in which the display control function 173 restricts accepting a change in the position of the second border line will now be explained. For example, the display control function 173 is set in such a manner that no change in the position of the second border line is accepted at position where borders of the right ventricular polar-map intersect with each other in a cross-shape, before the application of such a change. More specifically, if a change is applied to a border position at which borders intersect with each other in a cross-shape, and the cross-shape is changed to a T-shape, the mapping near the border position become spatially discontinuous in the right ventricular polar-map after the change in which the relative positional relations between the regions of interest are maintained, and gives an unnatural impression.

To explain using an example, in FIG. 5C, the border lines extending in the radial directions along the hinge 21 (at the position of one and a half o'clock) and the hinge 22 (at the position of six o'clock) both intersect with the circumferential border line indicating the level of the apex portion, in a cross-shape. Although not particularly illustrated, the same thing occurs in the second border lines at the corresponding positions in the SR image. If the position of the border between the local area denoted by the number 2 and the local area denoted by the number 3 is shifted in the circumferential direction in the SR image, the border line extending along the hinge 22 between the local area denoted by the number 6 and the local area denoted by the number 7 becomes discontinuous, and a T-shaped area is formed on the borders. In the example illustrated in FIG. 5C, the same can be said to the position of the border between the local area denoted by the number 4 and the local area denoted by the number 5. If the position of this border is shifted in the circumferential direction, the border line along the hinge 21 becomes discontinuous, and a T-shaped area is formed on the borders. Therefore, at a border position where a border line extending radially intersects with a border line extending circumferentially in a cross-shape, acceptance of a change in the position of the border line is restricted, and the positions of such border lines are kept fixed. Instead of restricting the acceptance of a change in the position of the border line, the display control function 173 may also use any other control for preventing any borders from appearing to be discontinuous in the right ventricular polar-map, before and after the change in the position of the second border line. For example, the display control function 173 may performs some control for making the discontinuity less noticeable through image processing, such as a smoothing and an interpolating process, so that no discontinuous border appears in the right ventricular polar-map before and after a change in the position of the second border line.

Second Embodiment

Explained in the first embodiment is an example in which a polar-map of a right ventricle is generated. Explained in a second embodiment is an example in which a polar-map of a left ventricle, as well as a polar-map of a right ventricle, are presented simultaneously.

Because the overall configuration of the ultrasound diagnostic apparatus according to the second embodiment is the same as the exemplary configuration illustrated in FIG. 1, except that the acquiring function 171, the generating function 172, and the display control function 173 have additional functions explained below, the explanations thereof are omitted herein.

The acquiring function 171 according to the second embodiment include the following function, in addition to the functions provided to the acquiring function 171 according to the first embodiment. In other words, the acquiring function 171 according to the second embodiment acquires the local function index values related to the left ventricle.

The generating function 172 according to the second embodiment includes the following function in addition to the functions provided to the generating function 172 according to the first embodiment. In other words, the generating function 172 according to the second embodiment also generates a functional image of the left ventricle, representing a distribution of the local function index values, using a medical model diagram of the left ventricle in which the left ventricle is developed onto a plane.

The display control function 173 according to the second embodiment includes the following function in addition to the functions provided to the display control function 173 according to the first embodiment. In other words, the display control function 173 according to the second embodiment displays the functional images of the right ventricle and the left ventricle simultaneously on the display 103, side by side with respect to each other.

Figure 14A:
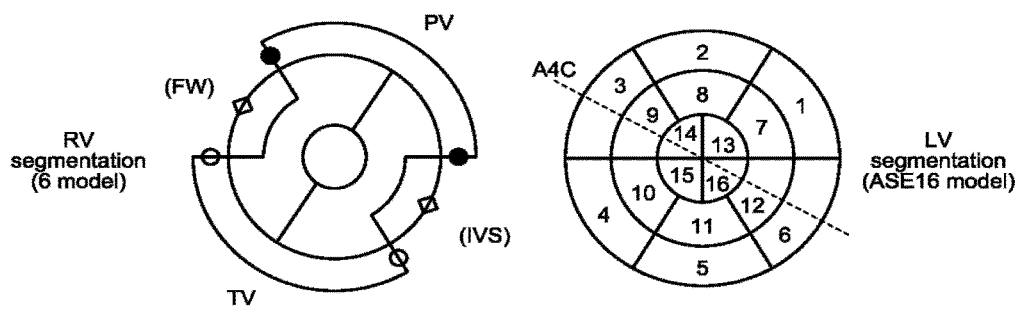
FIG. 14A is a schematic for explaining a second embodiment.
Figure 14B:
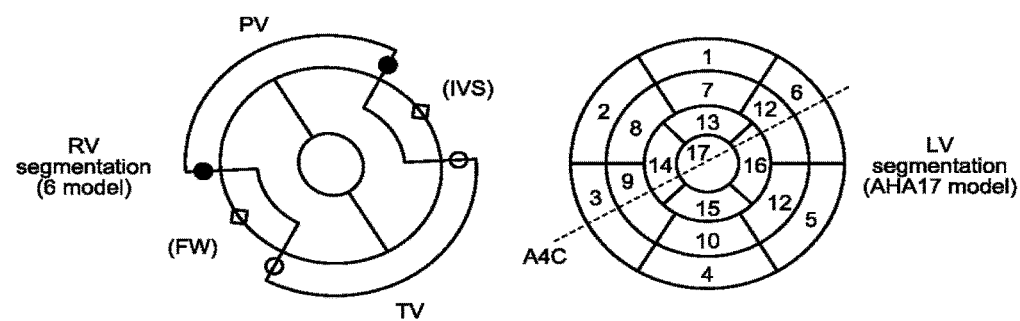
FIG. 14B is another schematic for explaining the second embodiment.

Between the customary ASE-recommended left ventricular segment model (16-segment model) and AHA-recommended left ventricular segment model (17-segment model), corresponding wall areas represented in the resultant polar-maps are shifted by some rotational angle. FIGS. 14A and 14B are schematics for explaining the second embodiment. The schematic on the right in FIG. 14A represents the ASE-recommended, customary left ventricular segment model, and the schematic on the right in FIG. 14B represents the customary AHA-recommended left ventricular segment model. Using an apical four-chamber view (A4C) as a reference cross section, in the ASE-recommended left ventricular segment model illustrated in the schematic on the right in FIG. 14A, the A4C corresponds to the linear area passing through the local areas denoted by numbers 3, 9, 14, 16, 12, 6. By contrast, in the AHA-recommended left ventricular segment model illustrated in the schematic on the right in FIG. 14B, the A4C corresponds to the linear area passing through the local areas denoted by numbers 3, 9, 14, 17, 16, 12, and 6. In the manner described above, with the ASE-recommended customary left ventricular segment model and the AHA-recommended customary left ventricular segment model, corresponding wall areas are represented at different rotational angles in the respective polar-maps.

To address this issue, the display control function 173 according to the second embodiment displays the polar-map of the right ventricle in a rotated manner so that the positional relation is matched with that represented in the polar-map of the left ventricle, based on the selected left ventricular segment model. For example, when selected is the AHA-recommended left ventricular segment model, the display control function 173 according to the second embodiment displays the right ventricular segment model illustrated in FIG. 5B in a manner rotated by a predetermined angle, as illustrated in the left schematic in FIG. 14B. When selected is the ASE-recommended left ventricular segment model, the display control function 173 according to the second embodiment keeps the right ventricular segment model illustrated in FIG. 5B with no rotation, as illustrated in the left schematic in FIG. 14A.

The display control function 173 according to the second embodiment may rotate the selected left ventricular segment model by a predetermined angle, instead of rotating the right ventricular segment model. In other words, when the functional image of the right ventricle and the functional image of the left ventricle are displayed simultaneously on the display 103, the display control function 173 according to the second embodiment presents at least one of the functional images of the right ventricle and the left ventricle in a manner rotated by a predetermined angle, depending on the type of segment model used for the medical model diagram of the left ventricle. Furthermore, in such a configuration, although not particularly illustrated, the display control function 173 may shift the positions of the respective segment models in a vertical direction so that the lines representing the positions of the A4C in the right and the left segment models extend along the same line, before displaying the functional images of the right ventricle and the left ventricle.

As described above, in the second embodiment, a polar-map enabling the positional relation of the right ventricle to be easily recognized is generated, and the polar-maps of the right ventricle and the left ventricle are displayed simultaneously in a manner retaining their positional relations. As a result, according to the second embodiment, the positional relation of the right ventricle and the positional relation of the left ventricle can be recognized easily.

Other Embodiments

The embodiments are not limited to those described above.

Process of Calculating Wall-Motion Index Values

Explained in the embodiment described above is an example in which the acquiring function 171 calculates the local wall-motion index values related to the right ventricular region from the volume data over a period of at least one cycle, but the embodiment is not limited thereto. For example, the acquiring function 171 may calculate the local wall-motion index values related to the cardiac right ventricular region, as the local function index values, by calculating the local wall-motion index values for each slice of the right ventricle based on a plurality of pieces of slice data including the cardiac right ventricular region over a period of at least one cycle, and by synthesizing the local wall-motion index values for each of the slices.

For example, there is a known technology, for the left ventricle, for synthesizing results of two-dimensional speckle-tracking (2DT) analyses using three longitudinal slices (an apical two-chamber view (A2C), an apical longitudinal view (A3C), and an apical four-chamber view (A4C)), and outputting the result as a polar-map of the left ventricle. Because the right ventricle has a more complex form, however, it is preferable for the acquiring function 171 to synthesize the 2DT results using a large number of, that is, more than three short-axis slices, e.g., about 10 slices, instead of using a plurality of longitudinal views.

Selection of Polar-Map Conditions

Among the conditions (1) to (4) of the polar-map described above, the combinations of the conditions (2) to (4) can be changed in any way by receiving a selection from a user, for example. The type of the right ventricular segment model used in the polar-map generating process may also be changed in any way by receiving a selection from the user.

Signs Indicating Mapping Relation of Connected Regions

Figure 15:
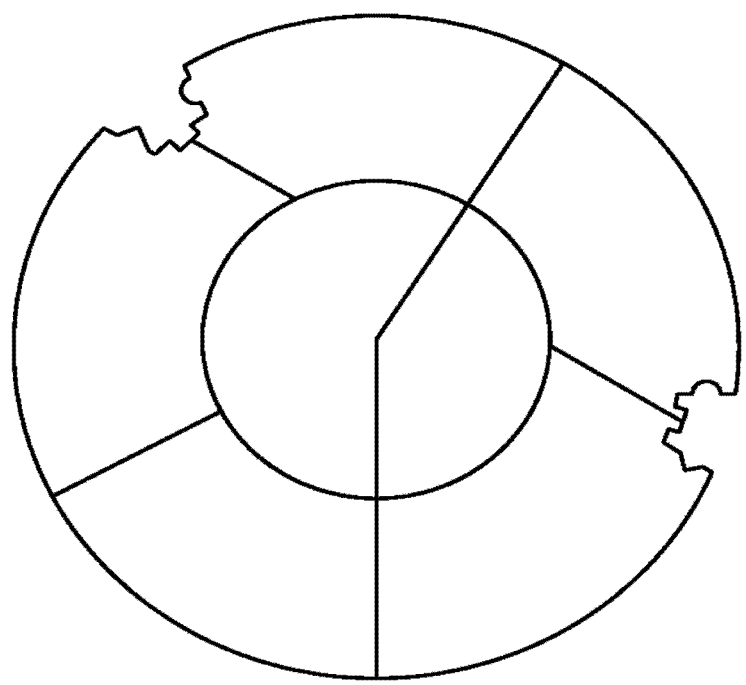
FIG. 15 is a schematic for explaining another embodiment.

Explained in the embodiments described above is an example in which white circle markers, black circle markers, and diamond markers are superimposed over the polar-map of the right ventricle, as marks indicating the mapping relation between the parts connected to each other, and as marks serving to satisfy the intention of the condition (4), as an example, but the embodiment is not limited thereto. FIG. 15 is a schematic for explaining another embodiment. For example, as illustrated in FIG. 15, a pair of markers having different shapes, e.g., a pair of orthogonal convex and concave markers, a pair of triangle and reversed triangle markers, or a pair of cap-shaped and cup-shaped markers may be superimposed over the polar-map of the right ventricle, as marks pointing to the corresponding regions that are connected with each other. Furthermore, numbers or characters, for example, may also be superimposed over the polar-map of the right ventricle, as the marks for representing the connecting relation.

The polar-map of the right ventricle or the left ventricle may be a still image related to a predetermined cardiac phase, or may be a moving image covering a period of one or more cardiac cycles.

Application to Medical Image Processing Apparatus

Explained in the embodiment described above is an example in which the polar-map generating process is performed by the ultrasound diagnostic apparatus 1, but the embodiment is not limited thereto. For example, the image data collected by the ultrasound diagnostic apparatus 1 may be transferred to an analysis apparatus such as a workstation performing image processing, and the analysis apparatus may be caused to execute the polar-map generating process.

Furthermore, explained in the embodiment described above is an example in which a wall-motion index is calculated using the image data collected by the ultrasound diagnostic apparatus 1, as the function index values of the right ventricle, but the embodiment is not limited thereto. For example, the function index values related to the right ventricular region map be calculated using image data collected by another type of medical diagnostic apparatus.

Figure 16:
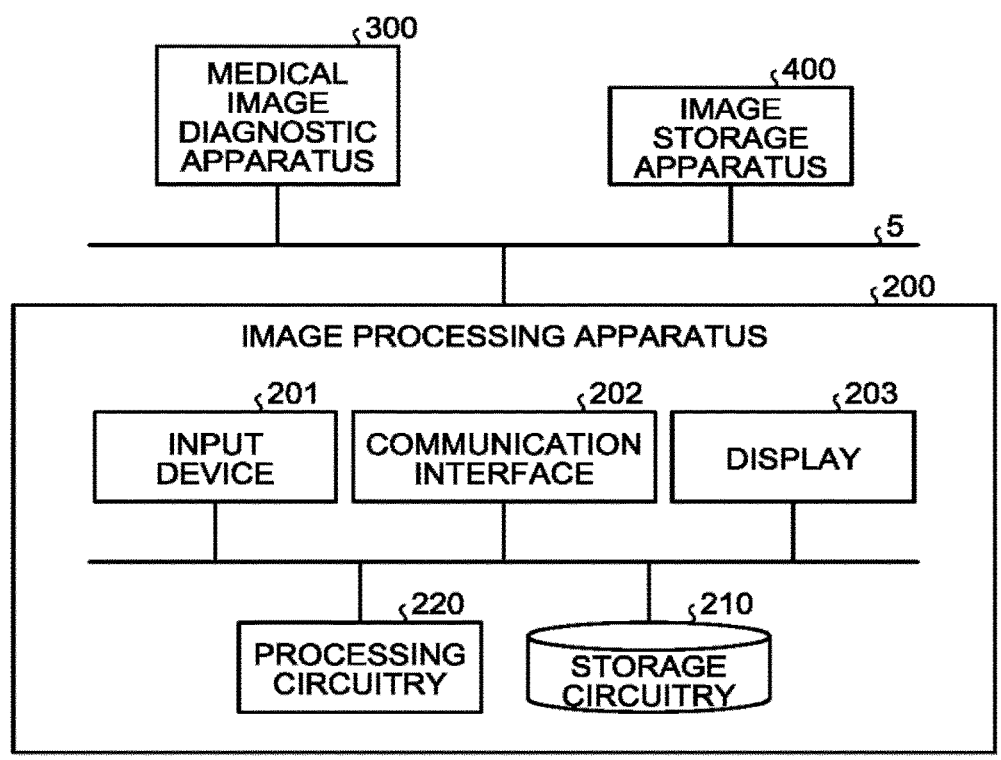
FIG. 16 is a schematic illustrating an exemplary configuration of the image processing system according to another embodiment.

FIG. 16 is a schematic illustrating an exemplary configuration of an image processing system according to another embodiment. As illustrated in FIG. 16, the image processing system according to another embodiment includes an image processing apparatus 200, a medical image diagnostic apparatus 300, and an image storage apparatus 400. The apparatuses illustrated in FIG. 16 are enabled to communicate with each other directly or indirectly, over an in-hospital local area network (LAN) 5 deployed in a hospital, for example. For example, when a picture archiving and communication system (PACS) is deployed in the image processing system, these apparatuses transmit and receive medical image data or the like with each other following the Digital Imaging and Communications in Medicine (DICOM) protocol.

In FIG. 16, the medical image diagnostic apparatus 300 collects three-dimensional medical image data, for example, and stores the collected three-dimensional medical image data in the image storage apparatus 400. The medical image diagnostic apparatus 300 corresponds to an ultrasound diagnostic apparatus, an X-ray diagnostic apparatus, an X-ray computed tomography (CT) apparatus, a magnetic resonance imaging (MRI) apparatus, a single photon emission computed tomography (SPECT) apparatus, a positron emission tomography (PET) apparatus, a SPECT-CT apparatus that is an integration of a SPECT apparatus and an X-ray computer tomography (CT) apparatus, a PET-CT apparatus that is an integration of a PET apparatus and an X-ray CT apparatus, a PET-MRI apparatus that is an integration of a PET apparatus and an MRI apparatus, or a group of apparatuses including these apparatuses in plurality, for example.

The image storage apparatus 400 is a database storing therein medical image data. Specifically, the image storage apparatus 400 stores the three-dimensional medical image data generated by various types of medical image diagnostic apparatus 300 in a storage unit locally provided. The three-dimensional medical image data stored in the image storage apparatus 400 is stored in a manner mapped to some supplementary information such as a patient ID, an examination ID, an apparatus ID, and a series ID.

Examples of the image processing apparatus 200 include a workstation and a PC used by physicians and ultrasonographers who work in the hospital in viewing the medical images. An operator of the image processing apparatus 200 acquires necessary three-dimensional medical image data from the image storage apparatus 400 by executing a retrieval using patient ID, an examination ID, an apparatus ID, or a series ID. Alternatively, the image processing apparatus 200 may receive the three-dimensional medical image data directly from the medical image diagnostic apparatus 300.

The image processing apparatus 200 includes an input device 201, a communication interface 202, a display 203, storage circuitry 210, and processing circuitry 220. The input device 201, the communication interface 202, the display 203, the storage circuitry 210, and the processing circuitry 220 are connected to one another.

The input device 201 is a pointing device such as a mouse or a pen tablet, a keyboard, or a trackball, for example, and receives various inputs to the image processing apparatus 200 from the operator. When used is a mouse, the operator can make an input using a mouse wheel. When used is a pen tablet, the operator can make an input with a flicking or a swiping operation. The communication interface 202 is a network interface card (NIC), for example, and establishes communication with other apparatuses. The display 203 is a monitor or a liquid crystal panel, for example, and displays various types of information.

The storage circuitry 210 is a hard disk or a semiconductor memory device, for example, and stores therein various types of information. For example, the storage circuitry 210 stores therein a plurality of processes executed by the processing circuitry 220.

The processing circuitry 220 is an electronic circuit such as a central processing unit (CPU) or a micro processing unit (MPU), or an integrated circuit such as an application specific integrated circuit (ASIC) or a field programmable gate array (FPGA), and controls the entire image processing apparatus 200.

The processing circuitry 220 executes the processes that are the same as those of the acquiring function 171, the generating function 172, and the display control function 173. For example, the processing circuitry 220 is a processor that implements the function corresponding to a computer program by reading the computer program from the storage circuitry 210 and executing the computer program. In other words, the processing circuitry 220 acquires, for example, a local function index value related to the right ventricle, as the same process executed by the acquiring function 171. At this time, the processing circuitry 220 acquires a local wall-motion index value related to the right ventricular region as the local function index value. The processing circuitry 220 may also acquire, as the local function index value, the information on the myocardial metabolism acquired by a nuclear medical diagnostic apparatus. The processing circuitry 220 may also acquire, as the local function index value, some composition information or blood flow information of the myocardial region acquired by an MRI diagnostic apparatus. The processing circuitry 220 may also acquire, as the local function index value, some function information of the myocardial region acquired by a CT diagnostic apparatus.

The processing circuitry 220 generates the functional image of the right ventricle representing a distribution of the local function index values using a medical model diagram of the right ventricle that is a model diagram in which the right ventricle is developed onto a plane and in which the blood inlet portion leading into the right ventricle and the blood outflow portion leading out from the right ventricle are plotted on the external circumference of the model diagram, in a manner separated from each other, as the same process executed by the generating function 172, for example.

The processing circuitry 220 causes the display 203 to display the functional image of the right ventricle, as the same process executed by the display control function 173, for example.

In the explanation of the embodiments, the units included in each of the apparatuses illustrated in the drawings are merely functional and conceptual representations, and do not need to be configured physically in the manner illustrated. In other words, the way in which each of the apparatuses is distributed or integrated are not limited to that illustrated in the drawings, and the entire apparatuses or some part of the apparatuses may be functionally or physically distributed or integrated into any units depending on various types of loads or usage conditions. Some or the entire processing functions executed in each of the apparatuses may be implemented as a CPU and a computer program parsed and executed by the CPU, or as a piece of hardware using a wired logic.

The control method explained in the embodiment above may be implemented by causing a computer, such as a personal computer or a workstation, to execute a control program prepared in advance. Such a control program may be distributed over a network such as the Internet. Furthermore, the control program may also be recorded in a computer-readable recording medium such as a hard disk, a flexible disk (FD), a compact disc read-only memory (CD-ROM), a magneto-optical (MO) disc, or digital versatile disc (DVD), and may be read from the recording medium and executed by the computer.

According to at least one of the embodiments described above, a polar-map enabling the positional relation of the right ventricle to be easily recognized can be generated.

While certain embodiments have been described, these embodiments have been presented by way of example only, and are not intended to limit the scope of the inventions. Indeed, the novel embodiments described herein may be embodied in a variety of other forms; furthermore, various omissions, substitutions and changes in the form of the embodiments described herein may be made without departing from the spirit of the inventions. The accompanying claims and their equivalents are intended to cover such forms or modifications as would fall within the scope and spirit of the inventions.

What is claimed is:

1. An ultrasound diagnostic apparatus comprising processing circuitry configured to:
    acquire local function index values related to a right ventricle;
    generate a functional image of the right ventricle representing a distribution of the local function index values, using a medical model diagram of the right ventricle, the medical model diagram being a model diagram in which the right ventricle is developed onto a plane, in which a blood inlet portion leading into the right ventricle and a blood outflow portion leading out from the right ventricle are plotted to positions that are separated on an external circumference side of the model diagram, and in which a crista supraventricularis is plotted between the blood inlet portion and the blood outflow portion in a direction along the external circumference of the model diagram, the functional image of the right ventricle being a functional image in which the blood inlet portion leading into the right ventricle and the blood outflow portion leading out from the right ventricle are plotted to positions that are separated on an external circumference side of the functional image, and in which the crista supraventricularis is plotted between the blood inlet portion and the blood outflow portion in a direction along the external circumference of the functional image; and
    cause a display to display the functional image of the right ventricle.

2. The ultrasound diagnostic apparatus according to claim 1, wherein the processing circuitry is configured to generate the functional image of the right ventricle in which the local function index values are mapped to corresponding positions of a region separating the blood inlet portion and the blood outflow portion, in the medical model diagram of the right ventricle.

3. The ultrasound diagnostic apparatus according to claim 1, wherein the processing circuitry is configured to generate, using a medical model diagram of the right ventricle in which a region separating the blood inlet portion and the blood outflow portion is dissected, and in which the blood inlet portion and the blood outflow portion are plotted to positions that are separated from each other, a functional image of the right ventricle in which (1) a part of a side of the blood inlet portion comprising a part of the region and (2) a part of a side of the blood outflow portion comprising the part of the region are rendered, and in which a same function index value is mapped to corresponding positions that would have been at a same position in the region had the region not been dissected.

4. The ultrasound diagnostic apparatus according to claim 1, wherein the processing circuitry is configured to generate the functional image of the right ventricle as a dissected image,
    the functional image of the right ventricle
    including a rendered image of a part of a side of the blood inlet portion comprising (1) a part of a region separating the blood inlet portion and the blood outflow portion, and (2) a part of a side of the blood outflow portion comprising the part of the region, and
    being appended with information for identifying corresponding positions that would have been at a same position in the region had the region not been dissected.

5. The ultrasound diagnostic apparatus according to claim 1, wherein the processing circuitry is configured to calculate local wall-motion index values related to a cardiac right ventricular region from a piece of volume data including the cardiac right ventricular region over a period of at least one cycle, as the local function index values.

6. The ultrasound diagnostic apparatus according to claim 1, wherein the processing circuitry is configured to calculate local wall-motion index values related to a cardiac right ventricular region, as the local function index values, by calculating the local wall-motion index values for each slice of the right ventricle based on a plurality of pieces of slice data including the cardiac right ventricular region over a period of at least one cycle, and by synthesizing the local wall-motion index values for each of the slices.

7. The ultrasound diagnostic apparatus according to claim 1, wherein the processing circuitry is configured to:
    acquire local wall-motion index values related to a cardiac right ventricular region as the local function index values,
    divide the cardiac right ventricular region into a plurality of regions of interest, and generate curves representing temporal changes of a wall-motion index value related to the respective regions of interest, cause the display to display the curves representing the temporal changes corresponding to the respective regions, and display, when a selection of an area of the functional image of the right ventricle corresponding to any one of the regions of interest is received, or when a selection of a curve representing a temporal change corresponding to any one of the regions of interest is received, the area of the functional image of the right ventricle and the curve representing the temporal change corresponding to the selected region of interest in a display form different from that used for areas of the functional image of the right ventricle and curves representing temporal changes corresponding to unselected region of interests.

8. The ultrasound diagnostic apparatus according to claim 1, wherein the functional image of the right ventricle is divided into a plurality of regions of interest by a first border line, the processing circuitry is further configured to generate a three-dimensional image that is based on the local function index values, and that has each position mapped with a corresponding position in the functional image of the right ventricle through a predetermined coordinate conversion, the three-dimensional image is divided into a plurality of regions of interest by a second border line, the functional image of the right ventricle is divided into the regions of interest by the first border line that remains unchanged even when the position of the second border line is changed, and the processing circuitry is configured to perform such control that no border in the functional image of the right ventricle becomes discontinuous, before and after the position of the second border line is changed.

9. The ultrasound diagnostic apparatus according to claim 7, wherein the processing circuitry is configured to calculate the local wall-motion index values through a process including a local tracking process.

10. The ultrasound diagnostic apparatus according to claim 7, wherein the processing circuitry is configured to calculate any of strain, area, displacement, ratio of change in the strain over time, ratio of change in the area over time, and ratio of change in the displacement over time, as the wall-motion index value.

11. The ultrasound diagnostic apparatus according to claim 7, wherein the processing circuitry is configured to display a border position by which the functional image of the right ventricle is divided into a plurality of regions of interest in the functional image of the right ventricle, and to change a display state of the border position depending on whether the corresponding region of interest is selected or not selected.

12. The ultrasound diagnostic apparatus according to claim 7, wherein the processing circuitry is further configured to cause the display to display a function index value related to the region of interest selected on the functional image of the right ventricle.

13. The ultrasound diagnostic apparatus according to claim 1, wherein the processing circuitry is further configured to:

acquire local function index values related to a cardiac left ventricle;

generate a functional image of the left ventricle representing a distribution of the local function index values related to the cardiac left ventricle, using a medical model diagram of the left ventricle in which the left ventricle is developed onto a plane, display, when the functional image of the right ventricle and the functional image of the left ventricle are displayed simultaneously on the display, at least one of the functional image of the right ventricle and the functional image of the left ventricle in a manner rotated at a predetermined angle, depending on a type of segment model used in the medical model diagram of the left ventricle.

14. A medical image processing apparatus comprising processing circuitry configured to:

acquire local function index values related to a right ventricle;

generate a functional image of the right ventricle representing a distribution of the local function index values, using a medical model diagram of the right ventricle, the medical model diagram being a model diagram in which the right ventricle is developed onto a plane, in which a blood inlet portion leading into the right ventricle and a blood outflow portion leading out from the right ventricle are plotted to positions that are separated on an external circumference side of the model diagram, and in which a crista supraventricularis is plotted between the blood inlet portion and the blood outflow portion in a direction along the external circumference of the model diagram, the functional image of the right ventricle being a functional image in which the blood inlet portion leading into the right ventricle and the blood outflow portion leading out from the right ventricle are plotted to positions that are separated on an external circumference side of the functional image, and in which the crista supraventricularis is plotted between the blood inlet portion and the blood outflow portion in a direction along the external circumference of the functional image, and cause a display to display the functional image of the right ventricle.

15. The medical image processing apparatus according to claim 14, wherein the processing circuitry is configured to acquire local wall-motion index values related to a cardiac right ventricular region as the local function index values.

16. The medical image processing apparatus according to claim 14, wherein the processing circuitry is configured to acquire information on myocardial metabolism collected by a nuclear medical diagnostic apparatus as the local function index values.

17. The medical image processing apparatus according to claim 14, wherein the processing circuitry is configured to acquire composition information or blood flow information of a myocardial region, the composition information or the blood flow information being acquired by a magnetic resonance imaging (MRI) diagnostic apparatus, as the local function index values.

18. The medical image processing apparatus according to claim 14, the processing circuitry is configured to acquire function information of a myocardial region, the function information being acquired by a computer tomography (CT) diagnostic apparatus, as the local function index values.

19. The medical image processing apparatus according to claim 14, wherein the processing circuitry is configured to acquire function information of a myocardial region, the function information being acquired by an ultrasound diagnostic apparatus, as the local function index values.

20. A medical image processing method comprising:

acquiring local function index values related to a right ventricle;

generating a functional image of the right ventricle representing a distribution of the local function index values using a medical model diagram of the right ventricle, the medical model diagram being a model diagram in which the right ventricle is developed onto a plane, in which a blood inlet portion leading into the right ventricle and a blood outflow portion leading out from the right ventricle are plotted to positions that are separated on an external circumference side of the model diagram, and in which a crista supraventricularis is plotted between the blood inlet portion and the blood outflow portion in a direction along the external circumference of the model diagram, the functional image of the right ventricle being a functional image in which the blood inlet portion leading into the right ventricle and the blood outflow portion leading out from the right ventricle are plotted to positions that are separated on an external circumference side of the functional image, and in which the crista supraventricularis is plotted between the blood inlet portion and the blood outflow portion in a direction along the external circumference of the functional image; and causing a display to display the functional image of the right ventricle.

21. The ultrasound diagnostic apparatus according to claim 1, wherein the crista supraventricularis has at least one notch, and a shape of the model diagram is circular.

22. The ultrasound diagnostic apparatus according to claim 21, wherein the at least one notch includes two notches.

23. The ultrasound diagnostic apparatus according to claim 22, wherein the two notches are opposed to each other.

24. An ultrasound diagnostic apparatus comprising processing circuitry configured to:

acquire local function index values related to a right ventricle;

generate a functional image of the right ventricle representing a distribution of the local function index values, using a medical model diagram of the right ventricle, the medical model diagram being a model diagram in which the right ventricle is developed onto a plane, and in which a blood inlet portion leading into the right ventricle and a blood outflow portion leading out from the right ventricle are plotted to positions that are separated without being in contact with each other on an external circumference side of the model diagram, the functional image of the right ventricle being a functional image in which the blood inlet portion leading into the right ventricle and the blood outflow portion leading out from the right ventricle are plotted to positions that are separated without being in contact with each other on an external circumference side of the functional image; and cause a display to display the functional image of the right ventricle, wherein the blood inlet portion and the blood outflow portion are plotted so as to be opposed to each other with a cardiac apex being interposed between the blood inlet portion and the blood outflow portion in the model diagram, and the blood inlet portion and the blood outflow portion are plotted so as to be opposed to each other with the cardiac apex being interposed between the blood inlet portion and the blood outflow portion in the functional image.

* * * * *